(12) United States Patent
Burn et al.

(10) Patent No.: US 9,078,330 B2
(45) Date of Patent: Jul. 7, 2015

(54) HIGHLY BRANCHED DENDRIMERS

(75) Inventors: Paul Leslie Burn, Brisbane (AU); Ifor David William Samuel, Fife (GB); Neil Cumpstey, Altrincham (GB)

(73) Assignees: ISIS INNOVATION LIMITED, Oxford (GB); THE UNIVERSITY COURT OF THE UNIVERSITY OF ST. ANDREWS, Fife (GB)

( * ) Notice: Subject to any disclaimer, the term of this patent is extended or adjusted under 35 U.S.C. 154(b) by 1160 days.

(21) Appl. No.: 11/886,450

(22) PCT Filed: Mar. 15, 2006

(86) PCT No.: PCT/GB2006/000915
§ 371 (c)(1),
(2), (4) Date: Dec. 13, 2007

(87) PCT Pub. No.: WO2006/097717
PCT Pub. Date: Sep. 21, 2006

(65) Prior Publication Data
US 2008/0211391 A1    Sep. 4, 2008

(30) Foreign Application Priority Data

Mar. 15, 2005 (GB) .................................. 0505320.2
Jul. 29, 2005 (GB) .................................. 0515640.1

(51) Int. Cl.
*C09K 11/06* (2006.01)
*H01L 51/54* (2006.01)
*H05B 33/14* (2006.01)
(Continued)

(52) U.S. Cl.
CPC ............ *H05B 33/14* (2013.01); *C07F 15/0033* (2013.01); *C08G 83/003* (2013.01); *C09K 11/06* (2013.01); *C09K 2211/1029* (2013.01); *C09K 2211/185* (2013.01); *H01L 51/0085* (2013.01);
(Continued)

(58) Field of Classification Search
None
See application file for complete search history.

(56) References Cited

U.S. PATENT DOCUMENTS

| 4,432,014 A | 2/1984 | Roos et al. |
| 5,150,006 A | 9/1992 | Van Slyke et al. |

(Continued)

FOREIGN PATENT DOCUMENTS

| EP | 1278061 | 1/2003 |
| EP | 1659129 A1 | 8/2004 |

(Continued)

OTHER PUBLICATIONS

U.S. Appl. No. 60/545,596, filed Jun. 2004.*
(Continued)

*Primary Examiner* — Marie R. Yamnitzky
(74) *Attorney, Agent, or Firm* — Quarles & Brady, LLP

(57) ABSTRACT

A dendrimer of formula (I): [DENDRON$^1$]$_x$-CORE-[B-[X]$_b$]$_a$ (I) wherein: CORE is a metal ion or a group containing a metal ion, or is a non-polymeric organic group; B is a phenyl ring; a is an integer of from 1 to 8; b is an integer of from 3 to 5; x is zero or an integer of from 1 to 7; each X is an aryl or heteroaryl ring, or is an at least partially conjugated dendritic molecular structure; each DENDRON$^1$ is an at least partially conjugated dendritic molecular structure; and wherein the dendrimer further comprises one or more surface groups; with the proviso that where CORE is a non-metallic core, then X is an at least partially conjugated dendritic molecular structure comprising at least one linking group.

23 Claims, 4 Drawing Sheets

(51) Int. Cl.
| | |
|---|---|
| C07F 15/00 | (2006.01) |
| C08G 83/00 | (2006.01) |
| H01L 51/00 | (2006.01) |
| H01L 51/50 | (2006.01) |

(52) U.S. Cl.
CPC .......... H01L 51/5012 (2013.01); Y02E 10/549 (2013.01)

(56) References Cited

U.S. PATENT DOCUMENTS

| | | | |
|---|---|---|---|
| 6,083,634 A | 7/2000 | Shi | |
| 6,461,747 B1 * | 10/2002 | Okada et al. ................. | 428/690 |
| 6,617,040 B2 | 9/2003 | Houser et al. | |
| 7,902,374 B2 * | 3/2011 | Lin et al. ...................... | 548/103 |
| 2004/0133004 A1 | 7/2004 | Stossel et al. | |
| 2004/0137263 A1 | 7/2004 | Burn et al. | |
| 2006/0251923 A1 * | 11/2006 | Lin et al. ...................... | 428/690 |

FOREIGN PATENT DOCUMENTS

| | | | |
|---|---|---|---|
| JP | 2003027048 A | 1/2003 | |
| JP | 2004292423 | 10/2004 | |
| JP | 2004355899 | 12/2004 | |
| JP | 2005093098 A | 4/2005 | |
| WO | 9921935 | 5/1999 | |
| WO | 02066552 | 8/2002 | |
| WO | 03079736 | 9/2003 | |
| WO | 2004020448 A1 | 3/2004 | |
| WO | WO 2004/020547 | 3/2004 | |
| WO | 2004026886 A2 | 4/2004 | |
| WO | WO 2004/029134 | 4/2004 | |
| WO | 2004101707 A1 | 11/2004 | |
| WO | 2004113468 | 12/2004 | |
| WO | 2005124890 | 12/2005 | |
| WO | WO 2006/093466 A1 * | 9/2006 | |

OTHER PUBLICATIONS

English Abstract for JP 2004355899 (Dec. 2004).
English Abstract for JP 2004292423 (Oct. 2004).
English Abstract for WO 2004/113468 (Dec. 2004).
Pogantsch et al., Adv. Mater. 2002, 14, No. 15, 1061-1064.
Becker et al., Synthetic Metals. 2002, 125, 73-80.
Marsitzky et al., J. Am. Chem. Soc. 2001, vol. 123, No. 29, 6965-6972.
Setayesh et al., J. Am. Chem. Soc. 2001, 123, 946-953.
Baldo et al., Appl. Phys. Lett. 1999, 75 (1), 4-6.
Yang et al., Appl. Phys. Lett. 2004, 84, 2476-2478.
Mitchell et al., J. Appl. Phys. 2004, 95, 2391-2396.
Halim et al., Adv. Mater. 1999, 11, 371-374.
Freeman et al., J. Am. Chem. Soc. 2000, 122, 12385-12386.
Adronov et al., Chem. Comm. 2000. 1701-1710.
Anthopolous et al., Adv. Mater. 2004, 16, 557-560.
Anthopolous et al., Appl. Phys. Lett. 2003. 82, 4824-4826.
Lo et al., Macromolecules. 2003, 36, 9721-9730.
Grushin et al., Chem. Commun. 2001, 1494-1495.
Coppo et al., Chem. Commun. 2004, 1774-1775.
Demas et al., The Journal of Phys. Chem. 1971, 75, 991-1024.
T. Anthopoulos et al., Influence of Molecular Structure on the Properties of Dendrimer . . . , 4 Organic Electronics 71-76 (2003).
J. Markham et al., Charge Transport in Highly Efficient Iridium Cored . . . , Journal of Applied Physics 95 (2), 438-445 (2004).
PCT Written Opinion/Search Report in PCT/GB2006/000915, dated Aug. 22, 2006.
Japanese Office Action in Japanese application 2008-501404 (Japanese counterpart) mailed Jan. 20, 2012, and English translation thereof.
M. Kimura et al., Selective Ligation to Sterically Isolated Metallophthalocyanines, 42 Inorganic Chem. 2821-2823 (2003).
C. Walsh et al., A Novel Method for the Peripheral . . . , 12 Chem. Mater. 287-289 (2000).
H. Sugimoto et al., Unusual Conformational Stability . . . , 14 J. Chem. Soc., Chem. Commun. 1411-1412 (1995).
J. T. Groves, et al., Preparation and Characterization of an (Acylperoxo)iron(III) Porphyrin, 26 Inorg. Chem. 785-786 (1987).
K. Suslick et al., A Bis-Pocket Porphyrin, 105 Am. Chem. Soc. 3507-3510 (1983).
S. Waybright et al., Organometallic Dendrimers Based On . . . , 124 J. Am. Chem. Soc. 8661-8666 (2002).
V. Hope et al., Synthese und Struktur . . . , 103 Angew. Chem. 726-727 (1991).
M. Thorn et al., Synthesis and Chemisry of Titancyclopentane . . . , 37 Am. Chem. Soc. 8630-8641 (1997).
H. Callot et al., Crystallographic Study and Ligand Substitution . . . , 28 Inorganic Chemistry 3633-3640 (1989).
G. Deacon et al., Rare Earth Complexes of Bulky . . . , 6 European Journal of Inorganic Chemistry 1505-1514 (2001).
C. Simpson et al., Nanosized Molecular Propellers by Cyclodehydrogenation . . . , 126 J. Am. Chem. Soc. 3139-3147 (2004).
X. Shen et al., Synthesis of Polyphenylene Dendrimers . . . , 126 J. Am. Chem. Soc. 5798-5805, (2004).
J. Zhang et al., A Colored Dendrimer as a New Soluble Support . . . , 42 Tetrahedon Letters 6683-6686 (2001).
Y. Pan et al., Synthesis of Light-Harvesting Dendrimers . . . , 1 Org. Biolmol. Chem. 4465-4470 (2003).
Y. Pan et al., Synthesis and Optical Properties . . . , 68 J. Org. Chem. 6952-6958 (2003).
Japanese Patent Office, Official Action, Application No. 2013-110488, Jun. 27, 2014, 8 pages, (with translation).
Japanese Patent Office, Office Action, Appeal No. 2013-9652 (Application No. 2008-501404), Aug. 29, 2014, 42 pages, (with translation).

* cited by examiner

Example 2, 32%

Example 1

Example 2

Example 3

R = 2-ethylhexyl

Fl =

HIGHLY BRANCHED DENDRIMERS

CROSS-REFERENCE TO RELATED APPLICATIONS

This application is a national phase application based on PCT/GB2006/000915 filed Mar. 15, 2006, and also claims priority based on GB 0505320.2 filed Mar. 15, 2005 and GB 0515640.1 filed Jul. 29, 2005.

FIELD OF THE INVENTION

This invention relates to dendrimers having highly branched dendrons and light-emitting devices containing them.

DESCRIPTION OF THE PRIOR ART

A wide range of luminescent small molecules and polymers are known and have been demonstrated as both light emitting and charge transporting materials in organic light emitting devices, in particular organic light-emitting diodes (OLEDs), also known as electroluminescent (EL) devices.

Intermolecular interactions play a key role in such OLEDs. Whilst strong intermolecular interactions between the electroactive chromophores are good for charge transport, they can be detrimental to light emission. Close interactions of emissive chromophores can lead to emission from excimers or aggregates leading to a change in emission colour and generally lower photoluminescence quantum yields (PLQYs).

Reports on OLEDs based on phosphorescent small molecules have generally shown that devices are more efficient when the phosphorescent molecule is a guest in a host matrix. At low concentration of phosphorescent molecule there are few intermolecular interactions of the emissive species and the device efficiency is high. However, in blended systems, whether evaporated or solution processed, there is always the issue of how evenly distributed the guest is in the host as localized high concentrations can lead to poor device performance. The most efficient method of controlling molecular interactions is by building in the control at the molecular level. This is difficult to do with small molecules, and with polymeric materials understanding the intermolecular interactions is complicated by the often complex polymer morphology.

In view of the above, dendrimer light-emitting diodes (DLEDs) have been developed in order to provide a degree of control at the molecular level. By judicious positioning of the dendrons this can be done without changing the emissive properties of the core chromophore. In particular, dendrimers having metal complex chromophores have been demonstrated to be effective in DLEDs. Suitable dendrimers are discussed in an earlier application of the current applicant, WO-A-02/066552.

There is a continuing need for further dendrimers which can be used in electroluminescent devices, and in particular for dendrimers which can provide good control at a molecular level in order to produce devices which are efficient and have other advantageous properties on a macromolecular level.

SUMMARY OF THE INVENTION

The present invention is particularly directed to dendrimers containing one or more at least partially conjugated, highly branched dendrons and in particular those containing solubilising moieties as surface groups. The use of such dendrimers forms another aspect of the present invention. Thus the invention provides dendrimers of formula (I):

$$[DENDRON^1]_x\text{-CORE-}[B\text{-}[X]_b]_a \qquad (I)$$

wherein:
CORE is a metal ion or a group containing a metal ion, or is a non-polymeric organic group;
B is a phenyl ring;
a is an integer of from 1 to 8;
b is an integer of from 3 to 5;
x is zero or an integer of from 1 to 7;
each X is the same or different and represents an aryl or heteroaryl ring, or represents an at least partially conjugated dendritic molecular structure comprising at least one branching group and optionally at least one linking group, the branching groups being selected from aryl and heteroaryl groups and nitrogen atoms, and the linking groups being selected from aryl, heteroaryl, vinyl and acetylenyl groups, said at least one branching group being bonded to three or more groups, and said at least one linking group being bonded to two groups, said dendritic molecular structure terminating at its distal points in aryl and/or heteroaryl groups;
DENDRON[1] represents an at least partially conjugated dendritic molecular structure comprising at least one branching group and optionally at least one linking group, the branching groups being selected from aryl and heteroaryl groups and nitrogen atoms, and the linking groups being selected from aryl, heteroaryl, alkyleneoxy, vinyl and acetylenyl groups, said at least one branching group being bonded to three or more groups, and said at least one linking group being bonded to two groups, said dendritic molecular structure terminating at its distal points in aryl and/or heteroaryl groups; and
wherein the dendrimer further comprises one or more surface groups;

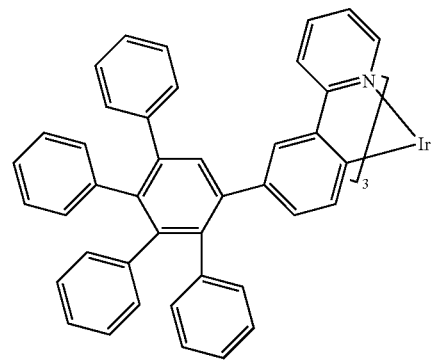

The CORE of the present dendrimers terminates in a single bond which is connected to group B (i.e. a phenyl ring) and, when one or more DENDRON[1] groups are attached, in a single bond which is connected to the first branching group of DENDRON[1]. This phenyl ring has at least three dendrons selected from aryl and/or heteroaryl groups and at least partially conjugated dendritic branches attached to it. Accordingly, the dendrimers of the present invention have a high degree of branching close to the emissive chromophore. Thus, the dendrimers can achieve shielding of the emissive chromophore at lower generation (generation level being determined by the number of sets of branching points). The highly branched conjugated dendrons used in the dendrimers of the present invention impart rigidity and give better control over the intermolecular interactions. This makes identifying the structure property relationships more straightforward.

It will be appreciated that when there is more than one dendron, the dendrons can be of the same or different generation (generation level is determined by the number of sets of branching points). It may be advantageous for at least one dendron to be of the second, or higher, generation to provide the required solution processing properties.

The invention also provides a semiconducting device which comprises at least one layer that contains a dendrimer as defined above. The invention also provides the use of a dendrimer as defined above as a light-emitting material. Also disclosed is a number of processes for preparing the dendrimers of the invention.

DETAILED DESCRIPTION OF THE INVENTION

Figure 1:
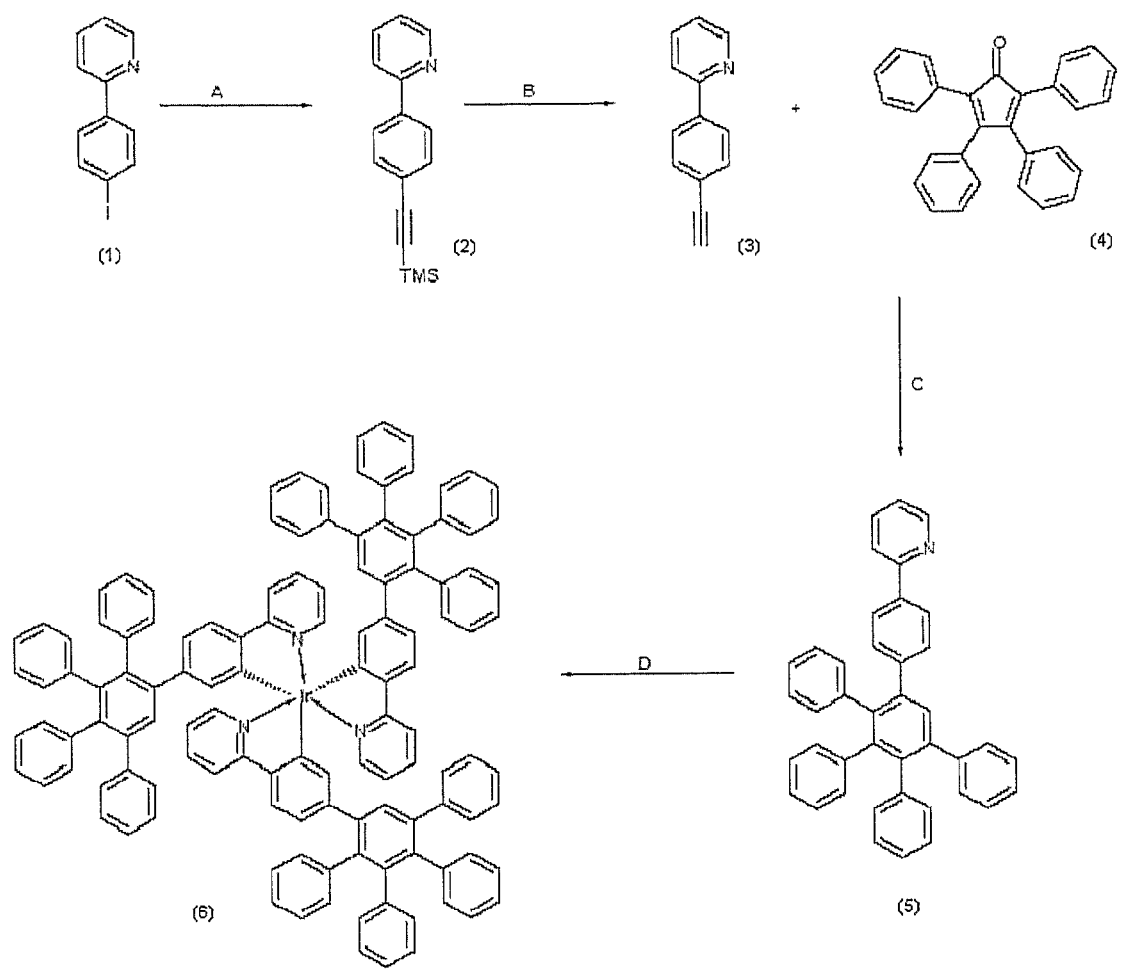
FIGS. 1, 2A and 2B show schemes for preparing dendrimers of the present invention.

It is to be understood that the term "metal ion" or "metal cation", as used herein, describes the charge state the metal would have without any ligands attached (the oxidation state). In the dendrimers of the invention that contain a metal cation the overall charge of the dendrimer is neutral and the metal-ligand bonding will have more or less covalent character depending on the metal and ligand involved.

It is to be understood that, in the context of the present invention, an organometallic dendrimer is one in which at least one organic ligand is coordinated to the metal. Such dendrimers do not necessarily contain a metal-carbon bond, because the organic ligand may be coordinated to the metal through an atom other than carbon, e.g. a nitrogen atom. However, dendrimers which contain at least one metal-carbon bond are preferred.

As used herein, the term "dendrimer" represents a structure such as the structure of formula (I) having a core and a number of dendrons attached to the core. At least one of the dendrons is a group of formula -[B-[X]$_b$]$_a$, i.e. a group comprising a group B which is further bonded to from 3 to 5 groups selected from (i) aryl and/or heteroaryl groups, and/or (ii) at least partially conjugated dendritic molecular structures.

As used herein, the phrase "at least partially conjugated" means that at least a portion of the dendron is made up of alternating double and single bonds or lone pairs, apart from the surface groups. Preferably all the dendrons or branching structures are made up of alternating single or double bonds or lone pairs; such a structure being termed a conjugated dendron. However this does not mean that the π system is fully delocalised. The delocalisation of the π system is dependent on the regiochemistry of the attachments.

As used herein the term "distal" means the part or parts of the molecule furthest from the core when following the bond sequence out from the core. It will be appreciated that due to the geometry of the bonds and moieties within a dendron a distal unit may be closer in space to the core than an earlier moiety in the dendron. The distal aryl and/or heteroaryl groups which may terminate the dendritic molecular structures described herein may be substituted, for example by one or more surface groups described below.

As used herein the term acetylenyl refers to acetylenyl groups that are divalent, vinyl refers to vinyl groups that are di- or trivalent, and aryl refers to aryl groups that are di-, tri- or multivalent.

As used herein the term $C_{1-15}$ alkyl is a linear or branched alkyl group or moiety containing from 1 to 15 carbon atoms such as a $C_{1-8}$ alkyl group or moiety or a $C_{1-4}$ alkyl group or moiety. Examples of $C_{1-4}$ alkyl groups and moieties include methyl, ethyl, n-propyl, i-propyl, n-butyl, i-butyl and t-butyl. For the avoidance of doubt, where two alkyl moieties are present in a group, the alkyl moieties may be the same or different.

As used herein, a $C_{2-15}$ alkenyl group or moiety is a linear or branched alkenyl group or moiety containing from 2 to 15 carbon atoms respectively such as a $C_{2-8}$ alkenyl group or moiety or a $C_{2-4}$ alkenyl group or moiety. For the avoidance of doubt, where two or more alkenyl moieties are present in a group, the alkenyl moieties may be the same or different.

As used herein, a halogen is typically chlorine, fluorine, bromine or iodine. It is preferably chlorine, fluorine or bromine.

As used herein the term amino represents a group of formula —NH$_2$. The term $C_{1-15}$ alkylamino represents a group of formula —NHR' wherein R' is a $C_{1-15}$ alkyl group, preferably a $C_{1-15}$ alkyl group, as defined previously. The term di($C_{1-15}$)alkylamino represents a group of formula —NR'R" wherein R' and R" are the same or different and represent $C_{1-15}$ alkyl groups, preferably $C_{1-6}$ alkyl groups, as defined previously. As used herein the term amido represents a group of formula —C(O)NH$_2$.

As used herein the term aryl refers to $C_{6-14}$ aryl groups which may be mono- or polycyclic, such as phenyl, naphthyl and fluorenyl. An aryl group may be unsubstituted or substituted at any position. Unless otherwise stated, it carries 0, 1, 2 or 3 substituents. Preferred substituents on an aryl group include halogen, $C_{1-15}$ alkyl, $C_{2-15}$ alkenyl, —C(O)R wherein R is hydrogen or $C_{1-15}$ alkyl, —CO$_2$R wherein R is hydrogen or $C_{1-15}$ alkyl, hydroxy, $C_{1-15}$ alkoxy, $C_{2-15}$ alkenyloxy, $C_{1-15}$ alkylthio, $C_{2-15}$ alkenylthio, $C_{1-6}$ haloalkyl, $C_{2-15}$ haloalkenyl, $C_{1-15}$ haloalkoxy, $C_{2-15}$ haloalkenyloxy, amino, $C_{1-15}$ alkylamino, di($C_{1-15}$)alkylamino, $C_{6-14}$ aryloxy, —O$_2$SR wherein each R is the same or different and represents $C_{1-15}$ alkyl or $C_{2-15}$ alkenyl, —SiR$_3$ wherein each R is the same or different and represents hydrogen, $C_{1-15}$ alkyl or $C_{2-15}$ alkenyl, $C_{6-14}$ arylthio, $C_{6-14}$ aryl and 5- to 10-membered heteroaryl, and wherein the substituents are themselves unsubstituted or substituted. When the substituents are themselves substituted, suitable substituents on the substituents include 1, 2, 3 or 4 groups selected from $C_{1-15}$ alkyl, $C_{2-15}$ alkenyl, $C_{1-15}$ alkoxy, $C_{2-15}$ alkenyloxy, hydroxy and halogen. Particularly suitable are 1 or 2 groups selected from $C_{1-8}$ alkyl, $C_{2-8}$ alkenyl, $C_{1-8}$ alkoxy and $C_{2-8}$ alkenyloxy. In particular, when an aryl group is substituted by a $C_{6-14}$ aryl group or by a 5- to 10-membered heteroaryl group, these substituents are themselves unsubstituted or substituted by one or more substituents selected from $C_{1-15}$ alkyl, $C_{2-15}$ alkenyl, $C_{1-15}$ alkoxy and $C_{2-15}$ alkenyloxy. When an aryl group is substituted by groups other than $C_{6-14}$ aryl groups or 5- to 10-membered heteroaryl groups, the substituents are themselves preferably unsubstituted.

As used herein, a heteroaryl group is typically a 5- to 14-membered aromatic ring, such as a 5- to 10-membered ring, more preferably a 5- or 6-membered ring, containing at least one heteroatom, for example 1, 2 or 3 heteroatoms, selected from O, S and N. Examples include pyridyl, pyrazinyl, pyrimidinyl, pyridazinyl, furanyl, thienyl, pyrazolidinyl, pyrrolyl, oxadiazolyl, isoxazolyl, thiadiazolyl, triazinyl, thiazolyl, imidazolyl, pyrazolyl, oxazolyl, isothiazolyl, benzofuranyl, isobenzofuranyl, benzothiophenyl, indolyl, indazolyl, carbazolyl, acridinyl, purinyl, cinnolinyl, quinoxalinyl, naphthyridinyl, benzimidazolyl, benzoxazolyl, quinolinyl, quinazolinyl and isoquinolinyl.

When the heteroaryl group is a monocyclic heteroaryl group, preferred groups include thiophenyl, pyrrolyl, pyridyl, imidazolyl, triazinyl and triazolyl.

As used herein, references to a heteroaryl group include fused ring systems in which a heteroaryl group is fused to an aryl group. When the heteroaryl group is such a fused heteroaryl group, preferred examples are fused ring systems wherein a 5- to 6-membered heteroaryl group is fused to one or two phenyl groups. Examples of such fused ring systems are benzofuranyl, isobenzofuranyl, benzopyranyl, cinnolinyl, carbazolyl, benzotriazolyl, phenanthridinyl, benzothiophenyl, indolyl, indazolyl, benzimidazolyl, benzoxazolyl, quinolinyl, quinazolinyl and isoquinolinyl moieties.

A heteroaryl group may be unsubstituted or substituted at any position. Unless otherwise stated, it carries 0, 1, 2 or 3 substituents. Preferred substituents on a heteroaryl group include those listed above in relation to aryl groups. When a heteroaryl group is substituted by a $C_{6-14}$ aryl group or by a 5- to 10-membered heteroaryl group, these substituents are themselves unsubstituted or substituted by one or more substituents selected from $C_{1-15}$ alkyl, $C_{2-15}$ alkenyl, $C_{1-15}$ alkoxy and $C_{2-15}$ alkenyloxy. When a heteroaryl group is substituted by groups other than $C_{6-14}$ aryl groups or 5- to 10-membered heteroaryl groups, the substituents are themselves preferably unsubstituted.

As used herein, an alkoxy group is typically a said alkyl group attached to an oxygen atom. Similarly, alkenyloxy groups and aryloxy groups are typically a said alkenyl group or aryl group respectively attached to an oxygen atom. An alkylthio group is typically a said alkyl group attached to a thio group. Similarly, alkenylthio groups and arylthio groups are typically a said alkenyl group or aryl group respectively attached to a thio group. A haloalkyl or haloalkoxy group is typically a said allyl or alkoxy group substituted by one or more said halogen atoms. Typically, it is substituted by 1, 2 or 3 said halogen atoms. Haloalkyl and haloalkoxy groups include perhaloalkyl and perhaloalkoxy groups such as —$CX_3$ and —$OCX_3$ wherein X is a said halogen atom, for example chlorine or fluorine, as well as longer alkyl and/or alkoxy chains such as $C_{2-6}$ chains substituted by one or more halogen atoms.

Haloalkenyl and haloalkenyloxy groups are, by analogy, typically a said alkenyl or alkenyloxy group substituted by one or more said halogen atoms. Typically, it is substituted by 1, 2 or 3 said halogen atoms.

As described above, the invention provides a dendrimer of formula (I). In formula (I), B represents a phenyl ring. Use of a phenyl ring in this position, close to the CORE allows for a high degree of branching at low generation.

As described above, X may represent an at least partially conjugated dendritic molecular structure. Representative examples of such dendritic molecular structures can be found in PCT/GB02/00750, to which reference should be made. Possible X groups will now be described in more detail.

X Groups:

As noted above, each X is the same or different and represents an aryl or heteroaryl group, or represents an at least partially conjugated dendritic molecular structure comprising at least one branching group and optionally at least one linking group, the branching groups being selected from aryl and heteroaryl groups and nitrogen atoms, and the linking groups being selected from aryl, heteroaryl, vinyl and acetylenyl groups, said at least one branching group being bonded to three or more groups, and said linking groups being bonded to two groups, said dendritic molecular structure terminating at its distal points in aryl and/or heteroaryl groups. Where branching groups are described as being bonded to three or more groups, said groups can be branching or linking groups, or can be the aryl and/or heteroaryl rings which terminate the dendritic molecular structure. Where linking groups are described as being bonded to two groups, said groups can be branching or linking groups, or can be the aryl and/or heteroaryl rings which terminate the dendritic molecular structure.

When X represents an aryl group, it is preferably a $C_{6-14}$ aryl group such as a group selected from phenyl, fluorenyl and naphthyl. When X represents an aryl group it is preferably selected from phenyl and fluorenyl, more preferably it is phenyl.

When X represents a heteroaryl group, it is preferably a 5- to 10-membered heteroaryl group containing, within the ring, one, two or three heteroatoms selected from oxygen, sulphur and nitrogen. Exemplary heteroaryl groups include groups selected from pyridyl, thiophenyl, benzamidazolyl, carbazolyl, pyrimidinyl, pyrazinyl, pyridazinyl, quinolinyl, isoquinolinyl, quinoxalinyl, benzothiophenyl, phthalazinyl, quinazolinyl, imidazolyl, pyrazolinyl, oxazolinyl, oxadiazolinyl, triazolyl, triazinyl, thiadiazolyl, benzimidazolyl, benzoxazolyl, phenanthridinyl, furyl and benzothiophenyl. Most preferably, when X represents a heteroaryl group it is selected from groups such as thiophenyl. If the core contains iridium (III), it is preferred that the heteroaryl groups, if present, are not nitrogen-containing. When X is an aryl or heteroaryl group it is unsubstituted or substituted. Suitable substituents include those listed below as solubilising groups, and also those listed below as cross-linkable groups.

When X represents an at least partially conjugated dendritic molecular structure comprising at least one branching group and optionally at least one linking groups, the branching groups are selected from aryl and heteroaryl groups and nitrogen atoms. These groups are selected because they form groups which are at least trivalent and which are hence capable of bonding to three or more groups. One of said groups to which a branching group is bonded will be a branching or linking group of the previous generation, or the CORE of the dendrimer. The other two or more groups will be linking groups and/or branching groups of the next generation, or the aryl and/or heteroaryl groups which terminate the dendritic molecular structure. In the case of nitrogen, which is capable of bonding to up to four groups, when it is a branching group it will preferably bond to three groups only.

When a branching group is an aryl group, suitable groups include phenyl, naphthalene, anthracene and, where appropriate, substituted variations with the proviso that when the core contains iridium (III) the heteroaryl groups preferably do not comprise nitrogen. Preferably, when a branching group is an aryl group it is a phenyl ring. More preferably the branching group is a phenyl ring coupled at ring positions 1, 3 and 5. When a branching group is a heteroaryl group, suitable groups include pyridine, carbazolyl, triazole, triazine and, where appropriate, substituted variations. Carbazolyl and triazinyl are preferred. The branching groups are unsubstituted or substituted. Suitable substituents include those listed below as solubilising groups, and also those listed below as cross-linkable groups. It is preferred that the branching groups are not substituted by solubilising groups. Preferred branching groups are phenyl groups that do not have solubilising groups attached.

When X represents an at least partially conjugated dendritic molecular structure, the linking groups are selected from aryl, heteroaryl, vinyl and acetylenyl groups.

The linking groups are chosen because they are able to form divalent moieties which are capable of bonding to two groups. The groups to which said linking groups are bonded include other linking groups, branching groups and/or the aryl and/or heteroaryl groups which terminate the dendritic molecular structure.

When a linking group is an aryl group, suitable groups include $C_{6-14}$ aryl groups such as phenyl, naphthalenyl, anthracenyl, fluorenyl and, where appropriate, substituted variations. Preferably, when a linking group is an aryl group it is a phenyl or fluorenyl group. When the linking group is a phenyl ring, it is preferably coupled at ring positions 1 and 4. When the linking group is a fluorenyl ring, it is preferably coupled at ring positions 2 and 7. When a linking group is a heteroaryl group, suitable groups include pyridine, oxadiazole, thiophene and, where appropriate, substituted variations. Preferred heteroaryl linking groups include thiophene and pyridine.

The linking groups are unsubstituted or substituted. Suitable substituents include those listed below as solubilising groups, and also those listed below as cross-linkable groups. When a linking group is aryl, it is preferably an unsubstituted phenyl, or a fluorenyl which is unsubstituted or substituted by 1 or 2 surface groups at the 9-position. Preferred substituents for the fluorenyl group include 1 or 2, preferably 2, substituents selected from $C_{1-15}$ alkyl, $C_{1-15}$ alkoxy, $C_{1-15}$ haloalkyl, $C_{6-14}$ aryl. Alternatively, the two substituents on the 9-position of the fluorenyl group can together complete a 5- to 7-membered ring, such as a carbocyclyl ring. Preferably when a linking group is aryl it is unsubstituted phenyl or unsubstituted or substituted fluorenyl.

More than one of the moieties described as linking groups above can couple together to form larger linking groups. For example, a phenyl ring and a further phenyl ring can couple to form a biphenyl group which can itself be a linking group between two branching groups or between a branching group and an aryl or heteroaryl ring which terminates the dendritic molecular structure. When X represents an at least partially conjugated dendritic molecular structure then the dendritic molecular structure terminates at its distal points in aryl and/or heteroaryl groups. Preferred such aryl and/or heteroaryl groups are the same as the preferred groups for the embodiment in which X simply represents an aryl or heteroaryl group as defined above. Preferably these aryl and/or heteroaryl groups are substituted by one or more surface groups defined below.

In one embodiment it is preferred that at least one X group represents an at least partially conjugated dendritic molecular structure. For example, in one embodiment each X group represents an at least partially conjugated dendritic molecular structure.

DENDRON¹:

As shown in formula (I) it is not necessary that all dendrons attached to the core are identical to one another or are highly branched dendrons, provided that at least one dendron is a specified conjugated dendron as shown as part of one of formulae (I), (II), (III), (IV) or (V) (i.e. a dendron having a general structure -[B-[X]$_b$]$_a$).

As mentioned earlier, DENDRON¹ represents an at least partially conjugated dendritic molecular structure. The nature of DENDRON¹ is therefore similar to group X defined above when X represents an at least partially conjugated dendritic molecular structure, with the addition of alkyleneoxy as a possible linking group. In particular, groups such as —CH$_2$—O— can be used as linking groups. Thus, such dendrons may include ether-type aryl dendrons, for example where benzene rings are connected via a methyleneoxy link. Preferred values of DENDRON¹ are similar to the preferred values of group X discussed above when X is an at least partially conjugated dendritic molecular structure.

Thus, the dendrimers may be symmetrical (i.e. when x is zero and when each group -B-[X]$_b$]$_a$ is identical) or may comprise two or more dendrons which are non-identical (i.e. where the dendrimer is asymmetric). It is desirable that the number of dendronised ligands is sufficient to provide the required solution processing. In the case of the dendronised metal complexes where all the ligands are different the method of preparation may give rise to a statistical mixture of all complex types. This is not necessarily disadvantageous providing that the optical, electronic, and processing properties are satisfactory.

As described above, a is an integer of from 1 to 8. Preferably a is an integer of from 3 to 6, implying that the CORE is surrounded by from 3 to 6 dendrons of general formula -[B-[X]$_b$]$_a$. For example, a can be 3. In another embodiment, preferably when x is zero, a is an integer of from 3 to 6, more preferably 3.

Integer b can be from 3 to 5, but is preferably 4 or 5, more preferably 4. In this most preferred embodiment, therefore, the phenyl group (B) is bonded to the CORE and is then bonded to four other groups (which may be aryl or heteroaryl groups, or other branching or linking groups or a combination thereof).

It is preferred that x is zero or an integer of from 1 to 5, more preferably zero or an integer of from 1 to 3. When a is an integer of from 3 to 6, preferably x is zero. Most preferably x is zero and there are no DENDRON¹ groups present in the dendrimers of the invention. Accordingly, in a preferred embodiment there is provided a dendrimer of formula:

CORE-[B-[X]$_b$]$_a$     (II)

wherein CORE, B, a, b and X are as defined earlier in relation to formula (I).

In a further embodiment of the invention there is provided a dendrimer having the formula (III):

CORE-[B-[X$_1$-[X$_2$-[X$_3$-[X$_4$-[X$_5$]$_f$]$_e$]$_d$]$_c$]$_b$]$_a$     (III)

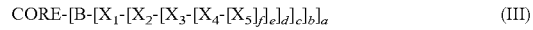

wherein:
a, b, CORE and B are as defined above in relation to formula (I) and formula (II);
c is zero or an integer of from 2 to 6;
when c is not zero, d is zero or an integer of from 2 to 6;
when d is not zero, e is zero or an integer of from 2 to 6;
when e is not zero, f is zero or an integer of from 2 to 6; and
each of X$_1$, X$_2$, X$_3$, X$_4$ and X$_5$, where present, is the same or different and represents a group of formula -[L$_g$-B']
wherein:
each L is the same or different and represents a linking group selected from aryl, heteroaryl, vinyl and acetylenyl groups;
g is zero or one, wherein when g is zero L is absent; and
each B' is the same or different and represents a group selected from aryl and heteroaryl groups and nitrogen atoms.

with the proviso that where CORE is a non-metallic core at least one group L is present.

Preferably each B' is the same or different and is selected from aryl and heteroaryl groups. More preferably each B' is the same or different and is a phenyl or fluorenyl group which are unsubstituted or substituted. The B' groups are unsubstituted or substituted, for example by one or more groups discussed below as surface groups. When the B' groups are not distal to the CORE, i.e. when they are part of a generation which is not the highest generation present in the dendrimer, then the B' groups are preferably unsubstituted. When the B' groups are distal to the CORE, i.e. when they are part of the highest generation present in the dendrimer, then they are preferably substituted by one or more groups discussed below as surface groups.

The linker groups (L), when present, are preferably the same or different and represent vinyl or $C_{6-14}$ aryl groups. More preferably the linker groups, when present, are vinyl, phenyl or fluorenyl groups, more preferably phenyl groups. The linker groups are unsubstituted or substituted by one or more groups listed below as surface groups. If the linker groups are substituted, preferred substituents include $C_{1-6}$ alkyl groups. Preferably the linker groups are unsubstituted.

Preferably integers c, d, e and f, when present, are 2, 3 or 4. More preferably integers c, d, e and f, when present are 2. The integer f may be zero while each of c, d and e is other than zero. When this occurs, the dendrimer is a $4^{th}$ generation dendrimer. Similarly, when integer e is zero but both of c and d is other than zero, the dendrimer is a $3^{rd}$ generation dendrimer. Likewise, when integer d is zero but c is other than zero, the dendrimer is a $2^{nd}$ generation dendrimer. When integer c is zero, the dendrimer is a $1^{st}$ generation dendrimer.

When the dendrimer has formula (III), it is preferred that $X_1$ is a $C_{6-14}$ aryl group (i.e. $X_1$ is -[$L_g$-B'] where g is zero and B' is $C_{6-14}$ aryl). More preferably, $X_1$ is a phenyl or fluorenyl group. Alternatively, it may be preferred that $X_1$ is -[$L_g$-B'] where g is one, L is $C_{6-14}$ aryl and B' is $C_{6-14}$ aryl. More preferably both L and B' are phenyl. In addition, in any one dendron the $X_1$ groups may be the same or different. For example, one or more $X_1$ groups may be those discussed above where g is zero, and one or more may be discussed above where g is one.

When present, $X_2$ is preferably a group of formula -[$L_g$-B'] wherein B' is a $C_{6-14}$ aryl group, most preferably a phenyl or fluorenyl group. The L group of $X_2$, when present, is preferably a phenyl, vinyl or fluorenyl group, more preferably a phenyl group.

Similarly, when present, each one of $X_3$, $X_4$ and $X_5$ is preferably a group of formula -[$L_g$-B'] wherein B' is a $C_{6-14}$ aryl group, most preferably a phenyl or fluorenyl group. The L group of the groups $X_3$, $X_4$ and $X_5$ when present, are preferably selected from a phenyl, vinyl and fluorenyl groups, and are more preferably phenyl groups.

In this embodiment it is also preferred that the HOMO-LUMO energy gap of CORE is lower than that of the conjugated moieties in the groups B, $X_1$, $X_2$, $X_3$, $X_4$ and $X_5$. The HOMO-LUMO energy gap of the conjugated moieties the groups B, $X_1$, $X_2$, $X_3$, $X_4$ and $X_5$ in the dendron may also decrease from the surface to the point of attachment to the core.

In a further embodiment of the invention there is provided a dendrimer of formula (IV):

CORE-[DENDRON²]ₐ     (IV)

wherein CORE and a are as defined earlier in relation to formula (I), DENDRON² is a group of formula -B-[X]ᵦ wherein B, X and b are as defined earlier in relation to formula (I), and wherein the links between adjacent branching points in said DENDRON are not all the same.

Such dendrimers of formula (IV) are called asymmetric dendrimers because they comprise either a single dendron having non-identical linking groups or alternatively two or more dendrons which are not identical. Similarly to the dendrimers of formulae (I) to (V), the dendrimers of formula (IV) can also comprise one or more surface groups as defined below.

Surface Groups and Other Substituents:

The dendrimers of the invention may comprise one or more substituents. Generally the substituents are chosen such that the dendrimers have increased solubility in the solvent in which they will be processed. Such groups are therefore termed "solubilising groups". When the solubilising groups are attached to the distal aryl or heteroaryl groups or the dendrons they are termed "surface groups". In particular, preferred surface groups are those which are capable of improving the solubility of the claimed dendrimers in solvents suitable for solution processing. Accordingly, suitable surface groups include those which result in the dendrimers having increased solubility in solvents such as tetrahydrofuran, toluene, chloroform, chlorobenzene, xylenes and alcoholic solvents such as methanol.

The surface groups are capable of changing the electronic properties of the aryl or heteroaryl moieties to which they are attached. The groups preferably impart good solubility to the dendrimers and may also contain moieties that allow patterning. The attachment position and number of the surface groups attached to the aryl and heteroaryl moieties is dependent on their structure and well known to those skilled in the art of organic chemistry. Suitable surface groups include those disclosed in PCT/GB02/00750, to which reference should be made for further details. Suitable surface groups include hydroxy, $C_{1-15}$ alkyl, $C_{2-15}$ alkenyl, amine, $C_{1-15}$ alkylamine, di($C_{1-15}$)alkylamine, —COOR wherein R is hydrogen or $C_{1-15}$ alkyl, $C_{1-15}$ alkoxy, $C_{2-15}$ alkenyloxy, $C_{6-10}$ aryloxy, —O₂SR wherein R is $C_{1-15}$ alkyl or $C_{2-15}$ alkenyl, —SiR₃ wherein each R is the same or different and represents hydrogen, $C_{1-15}$ alkyl or $C_{2-15}$ alkenyl, $C_{1-15}$ alkylthio, $C_{2-15}$ alkenylthio, $C_{6-10}$ arylthio, $C_{6-14}$ aryl and 5- to 10-membered heteroaryl, wherein the groups $C_{6-10}$ aryl and 5- to 10-membered heteroaryl, when present, are substituted with from one to five substituents which are themselves unsubstituted and are selected from $C_{1-15}$ alkyl, $C_{2-15}$ alkenyl, $C_{1-15}$ alkoxy and $C_{2-15}$ alkenyloxy.

Particularly preferred surface groups include $C_{1-15}$ alkyl, $C_{1-15}$ alkoxy, and substituted $C_{6-14}$ aryl groups where the substituents are selected from $C_{1-15}$ alkyl and $C_{1-15}$ alkoxy. When the surface groups are selected from substituted $C_{6-14}$ aryl groups, preferred aryl groups include phenyl and fluorenyl, more particularly substituted fluorenyl. Preferred substituents on the $C_{6-14}$ aryl groups include $C_{1-15}$ alkyl groups and $C_{1-15}$ alkoxy groups, particularly $C_{1-10}$ alkyl and $C_{1-10}$ alkoxy groups. For example, n-propyl, t-butyl, methoxy and ethoxy surface groups may be used as substituents on the $C_{6-14}$ aryl group, or straight or branched chain $C_8$ alkoxy groups such as 2-ethylhexyloxy. Preferably the substituents are selected from $C_{1-10}$ alkyl groups. Preferably the $C_{6-14}$ aryl group carries from one to four substituents, more preferably from one to three substituents, most preferably one or two substituents.

When the surface groups are selected from $C_{1-15}$ alkyl groups, $C_{1-10}$ alkyl groups are preferred, such as methyl and ethyl, and straight or branched chain propyl and butyl. For example, surface groups include n-propyl and t-butyl. When the surface groups are selected from $C_{1-15}$ alkoxy groups, $C_{1-10}$alkoxy groups are preferred, for example 2-ethylhexyloxy.

Different surface groups may be present on different dendrons or different distal groups of a dendron. Where t-butyl groups are the surface groups attached to phenyl rings it is preferable that more than one is attached to each of the distal phenyl units.

The surface groups can also be chosen such that the dendrimer can be patterned. For example, a crosslinkable group can be chosen, which can be crosslinked upon irradiation or by chemical reaction. Alternatively, the surface groups can comprise protecting groups that can be removed to leave crosslinkable groups. Accordingly, the dendrimers of the invention may also comprise one or more reactable groups which can be reacted in order to cross-link. Suitable cross-linking groups include oxetanes.

When a dendrimer of the invention is according to formula (I) or (II), it is preferred that the dendrimer comprises at least one surface or solubilising group described above. Preferably when X in formula (I) or (II) represents an at least partially conjugated dendritic molecular or branched structure, at least one surface group described above is bonded to an aryl and/or heteroaryl group which terminates the dendritic branched structure. Preferably when X is an aryl or heteroaryl ring, the aryl or heteroaryl ring bears at least one surface group described above.

Accordingly, the invention also provides a dendrimer of formula (V):

CORE-[B-([X]$_b$-[S]$_h$)]$_a$  (V)

wherein:
a, b, B, X and CORE are as defined earlier in relation to formula (I) or (II);
each S is the same or different and represents a surface group; and
h is an integer of from 1 to 200.

The surface groups used in the dendrimers of formula (V) may be the same as those defined above. Preferably, when X is a dendritic molecular structure, at least one S is bonded to an aryl and/or heteroaryl group which terminates the dendritic molecular structure.

It will be understood that the number of surface groups (represented by integer h) can vary widely. The number of surface groups will clearly depend upon the reactants used to prepare the dendrimers of the invention, and upon the generation of dendrimer which is produced. The higher the generation of dendrimer, the greater the possible number of surface groups present.

Generally, for a first generation dendrimer, h can be up to about 30, more preferably from 3 to 20. Generally, for a second generation dendrimer, h can be up to about 60, more preferably from 3 to 30. Generally, for a third generation dendrimer, h can be up to about 100, more preferably from 3 to 60. Generally, for a fourth generation dendrimer, h can be up to about 150, more preferably from 3 to 100. As the generation increases beyond the fourth generation, the number of surface groups increases dramatically.

The invention further provides a dendrimer of formula (VI):

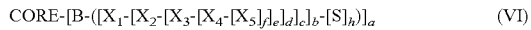

CORE-[B-([X$_1$-[X$_2$-[X$_3$-[X$_4$-[X$_5$]$_f$]$_e$]$_d$]$_c$]$_b$-[S]$_h$)]$_a$  (VI)

wherein
a, b, c, d, e, f, B, X$_1$, X$_2$, X$_3$, X$_4$, X$_5$ and CORE are as defined above in relation to formula (III);
each S is the same or different and represents a surface group; and
h is an integer of from 1 to 200.

Preferred S groups and preferred values of h are the same as defined previously in relation to formula (V). Other preferred features of this embodiment, for example the values of X$_1$ to X$_5$ and a to e are the same as for formula (III) discussed earlier.

Preferably when c is zero, h is from 1 to 30, more preferably from 3 to 20. Preferably when c is not zero but d is zero, h is from 1 to 60, more preferably from 3 to 30. Preferably when c and d are not zero but e is zero, h is from 1 to 100, more preferably from 3 to 60. Preferably when c, d and e are not zero but f is zero, h is from 1 to 150, more preferably from 3 to 100. Preferably when none of c, d, e or f is zero, h is from 1 to 200.

Core:

The core (denoted CORE in the formulae) is a metal ion or a group containing a metal ion, or is a non-polymeric organic group. The nature of the core is not critical to the invention, and can be chosen simply as a group to which a number of dendrons can be attached.

When the core is a non-polymeric organic group it can be luminescent (e.g. a conjugated group) or non-luminescent. Examples of cores which can be incorporated into luminescent chromophores include aryl and heteroaryl groups such as fluorenes, naphthalenes and porphyrin and perylene rings. As used herein, "non-polymeric" means that the core is not a polymeric group, although it may be in the form or a dimer, trimer or oligomer, or may be macrocyclic. When the core is in the form of an oligomer consisting of a number of units, it will preferably contain four or fewer units. Suitable units are single aryl or heteroaryl groups (e.g. a single fluorene unit). When it is a dimer, trimer or oligomer, it may comprise more than one such aryl or heteroaryl group, which are the same or different, bonded together and optionally substituted. For instance, suitable cores include difluorene, trifluorene and biphenyl groups as well as other combinations of single aryl and/or heteroaryl groups such as phenyl and thiophenyl. Examples of non-luminescent cores include aryl-substituted alkyl groups, such as tetraphenylmethane. While this is only one example of a suitable group it will be appreciated that a huge number of similar groups can function as cores provided they are capable of binding to a number of dendrons in order to form dendrimers according to the invention.

When the core is a metal ion or a group containing a metal ion, it typically comprises a metal cation and attached ligands; i.e. the ligands form part of the core itself. The metal is typically near the centre of the core and the core is typically luminescent. If it is not luminescent one or more of the dendrons should contain a luminescent group. It is preferred that the metal ion chromophore is sited at the core of the molecule, because then it will be relatively isolated from the core chromophores of adjacent molecules, which minimizes possible concentration quenching or triplet-triplet annihilation. The atoms or groups coordinating/binding to the metal typically form part of the core itself e.g. fac-tris (2-phenylpyridyl) iridium (III). In one embodiment, when the core is a metal ion or group it is preferably other than aluminium.

Preferred ligands which coordinate/bind to the metal include mono-, bi- and tri-dentate ligands, with bidentate ligands being preferred. Particular mention can be made of bidentate ligands which comprise a carbocyclic ring (which acts as a carbon donor) and a heterocyclic ring (which acts as a heteroatom donor, preferably a nitrogen donor). The carbocyclic rings may be chosen from aryl groups, for example phenyl. The heterocyclic rings may be chosen from heteroaryl groups, for example pyridine. The carbocyclic ring and heterocyclic ring are preferably directly linked by a single bond, for example as shown in a preferred ligand, 2-phenylpyridine. The dendron may be bound to either the carbocyclic ring or to the heterocyclic ring of such a bidentate ligand. Furthermore, the dendron may be bound to any position of the carbocyclic ring or heterocyclic ring, although for six-membered ring systems it is preferred that the dendron is bound to either the meta- or para-position relative to the bond between the carbocyclic or heterocyclic ring and the metal.

In a preferred embodiment, the CORE represents a group of formula $MW_wY_z$, in which M represents a metal cation, w represents an integer of 1 or more, each W to which a dendron is attached is the same or different and represents a mono-, bi- or tri-dentate coordinating group, z represents 0 or an integer of 1 or more, and each Y is the same or different and represents a coordinating group, the total of $(b·w)+(c·z)$ being equal to the number of coordination sites on M, wherein b is the number of coordination sites on W and c is the number of coordination sites on Y.

In this embodiment, preferably the metal cation is a cation of a d-block metal. More preferably it is iridium or rhenium, more preferably iridium.

The coordinating groups Y, when present, are neutral or charged chelated ligands which are not attached to dendrons and which serve to fulfil the coordination requirements of the metal cation. In one embodiment, neutral complexes are preferred. Preferably there are at least two ligands in a dendrimer, in which case w in this embodiment is an integer of 2 or more. Preferably there are at least two ligands present in a dendrimer, in which case the sum of w and z is 2 or more.

Suitable metals include:
  lanthanide metals: such as cerium, samarium, europium, terbium, dysprosium, thulium, erbium and neodymium;
  d-block metals, especially those in rows 2 and 3, that is, elements 39 to 48 and 72 to 80, such as iridium, platinum, rhodium, osmium, ruthenium, rhenium, scandium, chromium, manganese, iron, cobalt, nickel and copper; and
  main group metals of the Periodic Table, such as metals from Groups IA, IIA, IIB, IIIB e.g. lithium, beryllium, magnesium, zinc, aluminum, gallium and indium.

Suitable substituents Y, for rhenium in particular, include CO and halogen such as chlorine. For iridium dendrimers, the part of the ligands attached to the metal is preferably a nitrogen-containing heteroaryl, for example pyridine, attached to a (hetero)aryl where aryl can be a fused ring system, for example substituted or unsubstituted phenyl or benzothiophene. It should also be noted that the pyridine can also be substituted. Platinum dendrimers and especially platinum dendrimers with a porphyrin core with stilbene-based dendrons attached in the meso position are generally less preferred.

It will be appreciated that the light emission can be either fluorescent or phosphorescent depending on the choice of metal and coordinating groups.

Suitable coordinating groups for the f-block metals include oxygen or nitrogen donor systems such as carboxylic acids, 1,3-diketonates, hydroxy carboxylic acids, Schiff bases including acyl phenols and iminoacyl groups. As is known, luminescent lanthanide metal complexes require sensitizing group(s) which have the triplet excited energy level higher than the first excited state of the metal ion. Emission is from an f-f transition of the metal and so the emission colour is determined by the choice of the metal. The sharp emission is generally narrow, resulting in a pure colour emission useful for display applications. Due to the ability to harvest triplet excitons i.e. phosphorescence, the potential device efficiency can be higher than for fluorescent systems.

Main group metal complexes show ligand based, or charge transfer emission. The emission colour is determined by the choice of ligand as well as the metal. A wide range of luminescent low molecular weight metal complexes are known and have been demonstrated in organic light emitting devices [see, e.g., Macromol. Sym. 125 (1997) 1-48, U.S. Pat. No. 5,150,006, U.S. Pat. No. 6,083,634 and U.S. Pat. No. 5,432,014]. Suitable ligands for di- or trivalent metals include oxinoids e.g. with oxygen-nitrogen or oxygen-oxygen donating atoms, generally a ring nitrogen atom with a substituent oxygen atom, or a substituent nitrogen atom or oxygen atom with a substituent oxygen atom such as 8-hydroxyquinolate and hydroxyquinoxalinol, 10-hydroxybenzo(h)quinolinato, benzazoles, schiff bases, azoindoles, chromone derivatives, 3-hydroxyflavone, and carboxylic acids such as salicylato, amino carboxylates and ester carboxylates. The substituents are typically halogen, alkyl, alkoxy, haloalkyl, cyano, amino, amido, sulfonyl, carbonyl, aryl or heteroaryl on the (hetero) aromatic rings which may modify the emission colour.

The d-block metals form organometallic complexes with carbon and/or nitrogen donors such as porphyrin, 2-phenylpyridine, 2-thienylpyridine, benzo(h)quinoline, 2-phenylbenzoxazole, 2-phenylbenzothiazole, 5-phenyltriazole or 2-pyridylthianaphthene and iminobenzenes. The (hetero)aromatic rings can be substituted for example as for the R and X groups given above. The emission of d-block complexes can be either ligand based or due to charge transfer. For the heavy d-block elements, strong spin-orbit coupling allows rapid intersystem crossing and emission from triplet states.

Luminescence:

The dendrimers of the invention as described above are preferably luminescent in the solid state. The luminescence may result from the CORE and/or the dendrons. When an organometallic CORE is used, for example employing a core using a heavy d-block metal, the dendrimer is likely to be phosphorescent. The use of other metals or metal containing groups, e.g. $AlQ_3$, or the use of organic cores such as distyryl benzene, is likely to result in a fluorescent dendrimer. Preferably the dendrimers are phosphorescent in the solid state. The reason for this is that in fluorescent electroluminescent devices, many excitons form in the non-emissive triplet state, reducing the efficiency of light emission. Hence devices based on phosphorescent emitters, which can harvest the triplet excitons, have the potential for much higher efficiency than devices based on fluorescent emitters.

The dendrimer may have more than one luminescent moiety. In one instance the dendrimer incorporates at least two inherently luminescent moieties which moieties may or may not be conjugated with each other, wherein the dendron includes at least one of the said luminescent moieties. Preferably the luminescent moiety or moieties further from the core of the dendrimer have a larger HOMO-LUMO energy gap than the luminescent moiety or moieties closer to or partly or wholly within the core of the dendrimer. In another embodiment the HOMO-LUMO energy gap is substantially the same although the surface groups may change the HOMO-LUMO energy gap of the chromophores at the surface of the dendron. Sometimes in, say, the second generation dendrimer the surface group makes the chromophore at the distal end of the dendron of lower HOMO-LUMO energy compared to that of the next one in.

The relative HOMO-LUMO energy gaps of the moieties can be measured by methods known per se using a UV-visible spectrophotometer. One of the luminescent moieties may be, or be (partly or wholly) within, the core itself, which will thus preferably have a smaller inherent HOMO-LUMO gap energy than the other luminescent moiety or moieties in the dendron. Alternatively, or in addition, the dendrons themselves may each contain more than one luminescent moiety, in which case those further from the core will again preferably have larger inherent HOMO-LUMO gap energies than those closer to the core. In this case, the core itself need not be luminescent, although luminescent cores are generally preferred.

It is possible to control the electron affinity of the dendrimers by the addition to the chromophores of electron-withdrawing groups, where appropriate, for example cyano and sulfone which are strongly electron-withdrawing and optically transparent in the spectral region we are interested in. Further details of this and other modifications of the dendrimers can be found in WO-A-99/21935 to which reference should be made.

Processes:

The properties of dendrimers make them ideal for solution processing. The dendrimers can be dissolved in a solvent, the solution deposited onto a substrate, and the solvent removed to leave a solid film. Conventional solution-processing techniques can be used, for example spin-coating, printing (e.g. ink-jet printing) and dip-coating. A solid film containing the organometallic dendrimers can be either fluorescent or phosphorescent. The solid film is preferably formed on one side of a substrate and the thickness of the solid film is preferably less than 2 microns.

The dendrimers can be built in a convergent or divergent route, but a convergent route is preferred. With particular regard to organometallic dendrimers, the dendrons are attached to the appropriate ligands and these are subsequently attached to the metal cation to form the dendritic metal complex. Optionally other non-dendritic ligands can subsequently be attached to said complex. Alternatively a ligand with a suitably reactive functional group can be complexed to the metal ion, and then reacted with appropriately functionalised dendrons. In this latter method, not all ligands have to have the reactive functional groups, and thus this method allows the attachment of dendrons to some but not all of the ligands complexed to the metal.

The strategy for a sample convergent synthesis of a highly branched first generation organometallic dendrimer of the invention is shown in FIGS. 1 and 2. Taking FIG. 1 as an example, 2-(4-iodophenyl)pyridine (1) was prepared in a 40% yield by reaction of the mono-lithiated 1,4-diiodobenzene with 2-fluoropyridine. Trimethylsilylacetylene was then coupled with (1) under Sonogashira conditions to afford 2-(4-trimethylsilylethynylphenyl)pyridine (2) in an 89% yield. The acetylene was easily deprotected with either tetra-n-butylammonium fluoride in tetrahydrofuran or by treatment with aqueous potassium hydroxide in a methanol/dichloromethane mixture. Both methods gave 2-(4-acetylenylphenyl)pyridine (3) in an isolated yield of 80%. The dendronised ligand (5) was then formed by reaction of 3 with 2,3,4,5-tetraphenylcyclopentadienone (4). The reaction was heated at 220° C. for two to three hours using diphenyl ether as the solvent after which (5) was isolated in a 93% yield. The complexation of (5) to form the fac-tris(2-phenylpyridyl)iridium (III) cored dendrimer utilised the standard two step procedure. In the first step 2.5 equivalents of (5) was reacted with iridium trichloride trihydrate in aqueous 2-ethoxyethanol heated at reflux to give a mixture of the bis-iridium bis-chloro dimer and unreacted ligand. This mixture was then reacted with an excess of (5) in the presence of silver trifluoromethylsulfonate in diglyme at 130° C. to give, after purification, the desired dendrimer (6) in a 63% yield for the two steps. Gel permeation chromatography (GPC) showed that the dendrimer was mono-disperse and the facial nature of the dendrimer was confirmed by $^1$H NMR by comparison with spectra reported for other dendrimers with fac-tris(2-phenylpyridyl)iridium (III) cores.

In preferred embodiments of the processes described above the complex formed between the coordinating groups and the metal cation in step (b) is represented by formula $MX_xY_z$ as defined above.

Figure 2A:
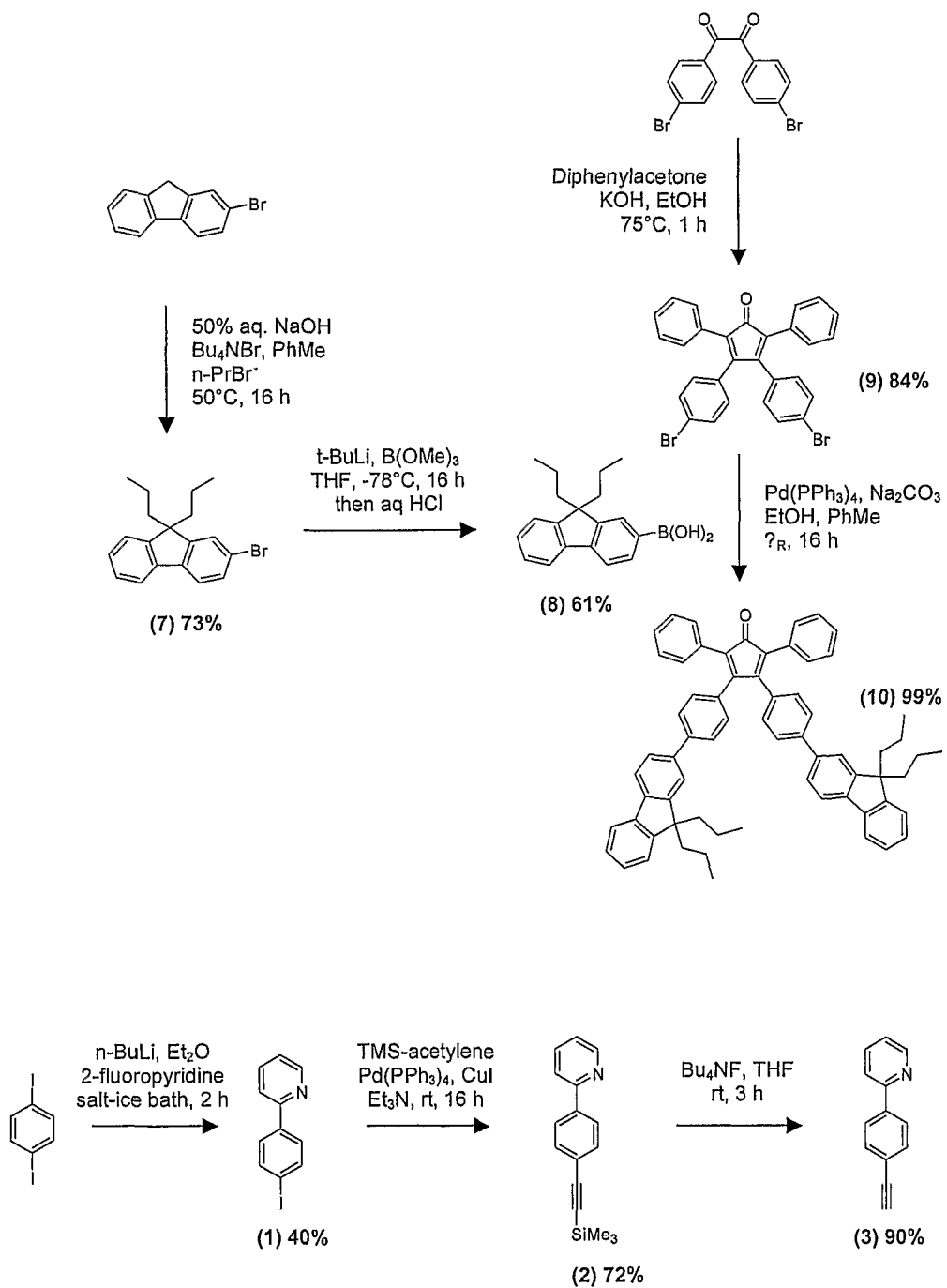

FIGS. 1 and 2 show exemplary methods for preparing dendrimers according to the invention. They can, however, be readily modified in order to prepare other dendrimers falling within the invention. A person skilled in the art will readily be able to prepare suitable starting materials to make dendrimers having, for example, different surface groups or different linking groups. As shown in Examples 3 and 4 which follow, a simple change of reactant can result in the dendrimers being attached to a different point of the core, or different surface groups being present at the distal ends of the dendrimers. With particular regard to the surface groups and with reference to FIG. 2A, different surface groups can be introduced into the dendrimers of the invention through an appropriate modification of the first step in the process (production of compound (7)). It will be appreciated that by suitable choice of reactants, different substituents can be introduced to the fluorenyl group. For example, use of n-BuBr in place of n-PrBr would result in the introduction of butyl substituents, rather than propyl substituents. Other surface groups can be introduced by analogous modifications of the process described in this scheme.

Figure 2B:
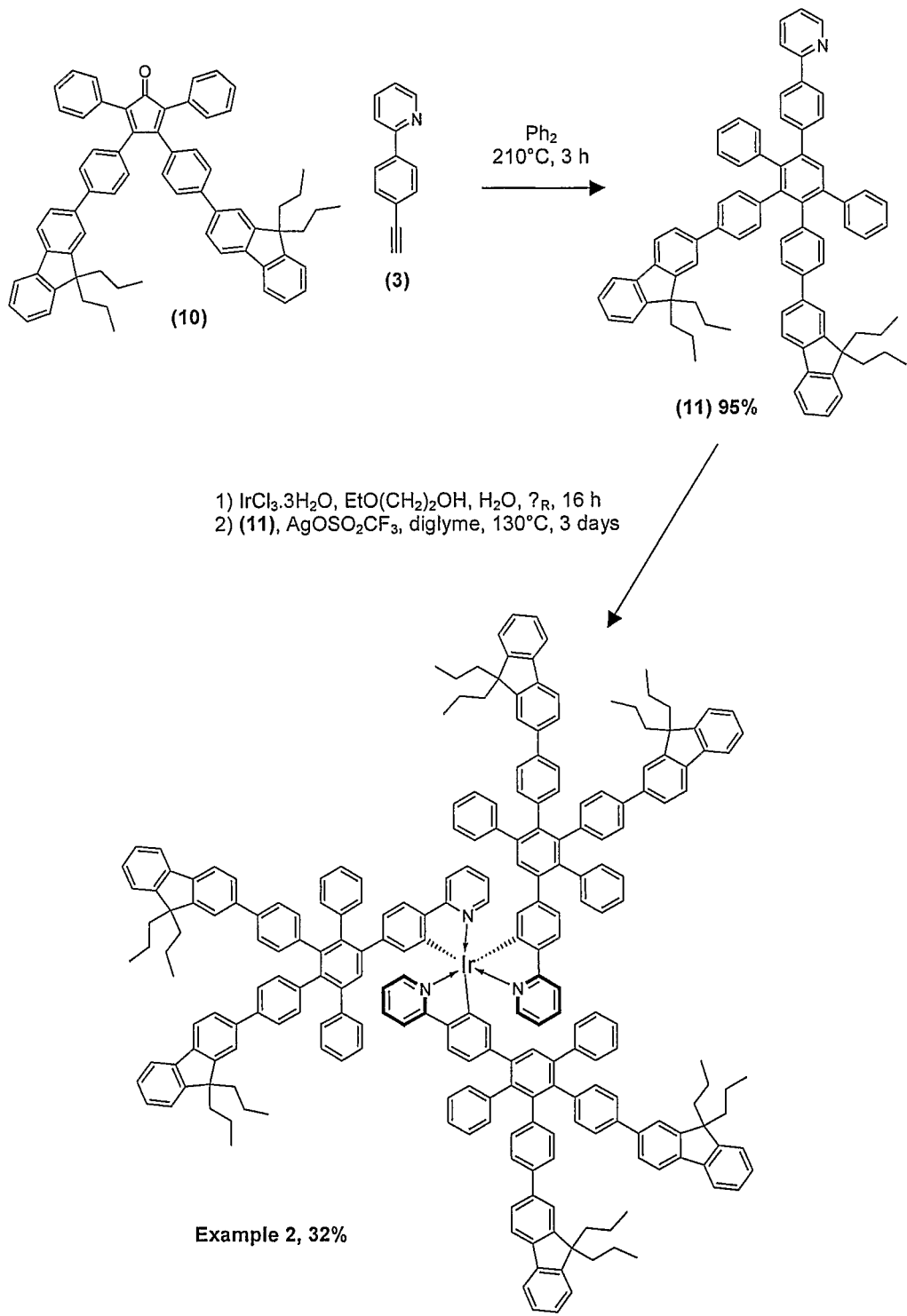
Figure 3:
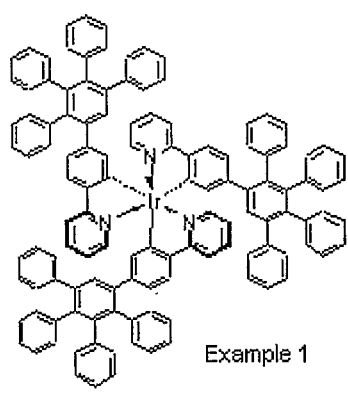
FIG. 3 shows exemplary dendrimers of the invention. The numbers used to describe the dendrimers corresponds to the Example number used later.
Figure 3:
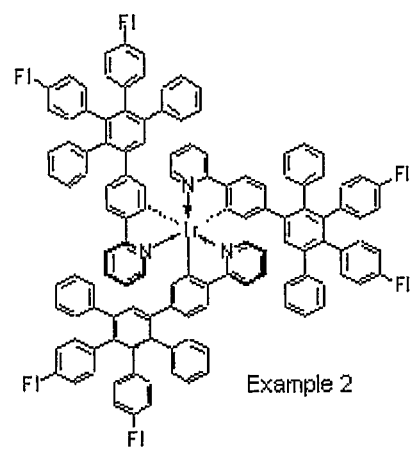
Figure 3:
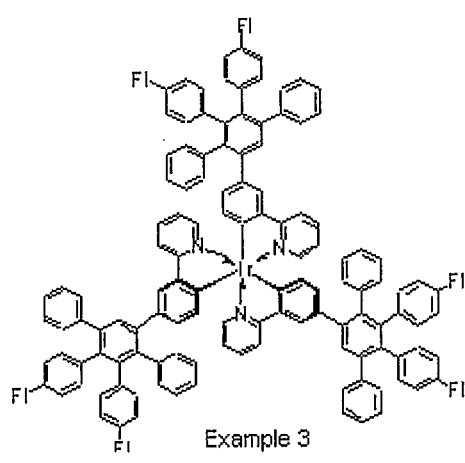
Figure 3:
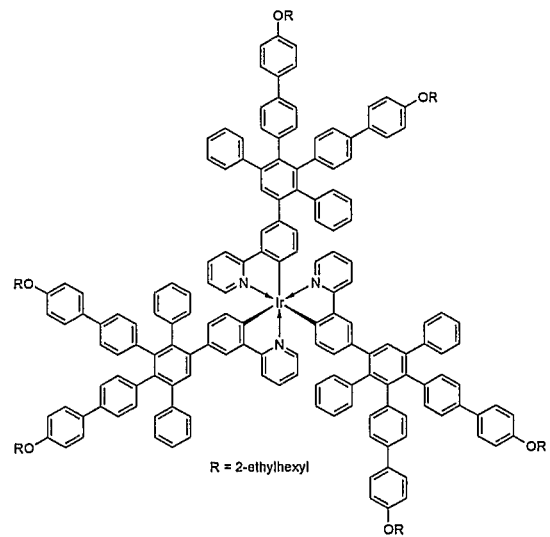
Figure 3:
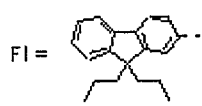

In the case of dendrimers of the invention comprising dendrons which are of higher generation and which have highly branched groups in these higher generations, a further strategy is required. By highly branched is meant that the branching group, as well as being bonded to the previous generation (either directly to the branching group of the previous generation or via a linking group), is bonded to three or more, preferably four of more, and most preferably four, other groups. These other groups may be linking groups, branching groups and/or the aryl and/or heteroaryl groups which terminate the dendritic molecular structure. For such dendrimers, it is first necessary to activate either the uncomplexed ligand (in the case of organometallic complexes) or the dendrimer itself. This can be achieved by bromination of the ligand or dendrimer. The product of this reaction is then reacted with acetylene, followed by reaction with cyclopentadienone in a semi-convergent, semi-divergent strategy. In the case of dendrimers of the invention comprising dendrons which are of higher generation but have lower branched groups in these higher generations, another strategy is employed. A first generation dendron is first reacted with boronic acid, and is subsequently reacted with 2,5-diphenyl-3,4-bis(4'-bromophenyl)cyclopentadienone, in a similar way to the reaction of (8) with the same compound as shown in FIG. 2A. The product of the reaction is then reacted via a Diels-Alder reaction in an analogous manner to the reaction of (10) and (3) as shown in FIG. 2B to produce the dendronised ligand, which is finally complexed to the metal to form the dendrimer of the invention in a convergent strategy.

Devices:

The dendrimers of the present invention may be used in a number of semiconducting devices. The dendrimer can be present in the semiconducting devices in the form of a layer or as part of a layer. Exemplary devices include light-emitting devices, photodiodes, solar cells, field effect transistors and solid state triodes. Preferably the devices in which the dendrimers of the invention are incorporated are light emitting devices (LEDs) and in particular organic light-emitting diodes also known as electroluminescent devices.

The dendrimers of the present invention may be used in a number of semiconducting devices. The dendrimer can be present in the semiconducting devices in the form of a layer or as part of a layer. Exemplary devices include light-emitting devices, photodiodes, solar cells, field effect transistors and solid state triodes. Preferably the devices in which the dendrimers of the invention are incorporated are light emitting devices (LEDs) and in particular organic light-emitting diodes also known as electroluminescent devices.

When the dendrimers of the invention are employed in light emitting devices, it is preferred that the dendrimer is present in the light emitting layer. The dendrimers may be present in such layers as essentially neat films of said dendrimers, or in the form of blends. In the discussion which follows, while the ranges are given in terms of weight percentage of the dendrimer, it will be appreciated that the number of moles of said dendrimer will vary too. In particular, for higher generation dendrimers a higher weight percentage will be required in order to provided a specific number of moles. In the case of phosphorescent organometallic dendrimers, it is important to achieve the optimum weight percentage of metal in the devices of the invention. The weight percentage of such dendrimers required to provide a certain amount of metal will clearly be dependent upon their generation and, ultimately, their total molecular weight.

The amount of dendrimer which can be present in the light emitting layer can vary considerably. For example, the dendrimer can be present in an amount of from about 5 to about 100 wt %.

In one embodiment, the light emitting layer may consist essentially of a dendrimer of the invention in the form of a homogeneous layer. Small amounts of other substances may be present in such layers, for example impurities or additives which improve the film-forming properties of the dendrimer. However, in this embodiment these other substances are preferably present in a small amount, for example less than about 5 wt %, more preferably less than about 3 wt %, for example less than about 1 wt %.

In another embodiment, the dendrimer is blended with another material and is present at a lower level, such as at a level of from 10 to about 80 wt %, more preferably from 10 to about 50 wt %, such as around 20 wt %. The dendrimer in such blends may be phosphorescent in the solid state.

The other material present in the blend may comprise one or more other dendrimers and/or polymers and/or molecular materials. For example, it has been found that it is advantageous to blend the dendrimer with a charge transporting material. In particular it has been found that the presence of a hole-transporting and/or a bipolar material and/or electron transporting material is advantageous. In a further embodiment the bipolar material should contain carbazole units. Preferably the other material is a small molecular material, with molecules such as 4,4-di(N-carbazole)biphenyl (CBP) being preferred. Another embodiment has one or more of each type of charge transporting material.

In another embodiment, the light emitting layer comprises a blend of dendrimers according to the invention. For example, the light emitting layer may comprise a blend of a first dendrimer of the invention wherein CORE is a metal ion or group containing a metal ion, and a second dendrimer of the invention wherein CORE is a non-polymeric organic group, and wherein the dendrons of the first dendrimer and second dendrimer have the same dendritic structure. Preferably the first and second dendrimers have the same structure in terms of the number and nature of the dendrons surrounding the CORE, yet the CORE for the first dendrimer is metallic or organometallic, and the CORE for the second dendrimer is non-metallic. Preferably the first dendrimer is phosphorescent in the solid state and the second dendrimer is luminescent in the solid state.

In general, the higher the generation of the dendrimer of the invention and/or the higher the number of dendrons present in the dendrimer, the more the CORE will be shielded from intermolecular interactions. As a result, the dendrimer can be used at higher levels in the light emitting layer without lowering the PLQY. Conversely, the lower the generation of the dendrimer of the invention and/or the lower the number of dendrons present in the dendrimer, the more the CORE will be exposed to intermolecular interactions. As a result, the dendrimer will need to be employed at lower levels in order to prevent quenching. Preferably, for the dendrimer to be used at a level of 50 wt % or more, it should have four or more dendrons and/or be 3rd generation or higher. Dendrimers of lower generation (i.e. 1st or 2nd generation) and/or with 3 or fewer dendrons will preferably be used at levels lower than 50 wt %.

Devices of the invention may comprise any additional components which are conventional in the art. For example, the device may additionally comprise at least one charge transporting and/or injecting layer.

The devices may be made by conventional processes. For example, the layer containing the dendrimer may be deposited by solution processing. Conventional solution processing techniques such as spin coating, printing, and dip-coating can be used to deposit the dendrimer layer. In a typical device a solution containing the dendrimer is applied over the transparent electrode layer, the solvent evaporated, and then subsequent layers applied. The thickness of the dendrimer-containing film is typically 10 nm to 1000 nm, preferably less than 200 nm, more preferably 30-120 nm.

In another embodiment, it has been found that it is advantageous to blend the dendrimer with a charge transporting material. In particular it has been found that the presence of a hole-transporting and/or a bipolar material and/or electron transporting material is advantageous. In a further embodiment the bipolar material should contain carbazole units. Another embodiment has one or more of each type of charge transporting material.

The dendrimers of the invention can be incorporated into an LED in a conventional manner. In its simplest form, an organic light emitting or electroluminescent device can be formed from a light emitting layer sandwiched between two electrodes, at least one of which must be transparent to the emitted light. Such a device can have a conventional arrangement comprising a transparent substrate layer, a transparent electrode layer, a light emitting layer and a back electrode. For this purpose the standard materials can be used. Thus, typically, the transparent substrate layer is typically made of glass although other transparent materials such as PET, can be used.

The anode, which is generally transparent, is preferably made from indium tin oxide (ITO) although other similar materials including indium oxide/tin oxide, tin oxide/antimony, zinc oxide/aluminum, gold and platinum can also be used. Conducting polymers such as PANI (polyaniline) or PEDOT can also be used.

The cathode is normally made of a low work function metal or alloy such as Al, Ca, Mg, Li, or MgAl or optionally with an additional layer of LiF. As is well known, other layers may also be present, including a hole transporting material and/or an electron transporting material. When the dendrimer is a phosphorescent emitter, it has been found that it is particularly beneficial to have a hole-blocking/electron-transporting layer between the light emitting dendrimer layer and the cathode. In an alternative configuration, the substrate may be an opaque material such as silicon and the light is emitted through the opposing electrode. There may also be a layer between the light emitting layer and the anode.

The invention will be described in the Examples which follow.

EXAMPLES

The structures of the compounds were confirmed by the standard spectroscopic methods and are reported in detail in N. Cumpstey (DPhil Thesis, University of Oxford, 2006).

Preparative Example 1

2-(4-Iodophenyl)pyridine (1)

A solution of 1,4-diiodobenzene (46.8 g, 142 mmol) in dry ether (450 mL) under argon was cooled in a salt-ice bath. n-Butyllithium (2.0 M in pentane, 72 mL, 142 mmol) was added, and the solution was stirred for 10 minutes. 2-Fluoropyridine (13 mL, 150 mmol) was added and the reaction was allowed to warm to room temperature over 2 hours. Water (500 mL) was added and the organic layer was separated. The aqueous layer was extracted with ether (3×200 mL) and the combined organic layers were washed with brine (1000 mL), dried over anhydrous magnesium sulfate, filtered, and the solvent completely removed. The residue was purified in two steps; first by column chromatography over silica using a dichloromethane/light petroleum mixture (1:1) followed by recrystallisation of the main fraction from a dichloromethane/light petroleum mixture to give (1) (17.0 g, 40%).

Preparative Example 2

2-(4-Trimethylsilylethynylphenyl)pyridine (2)

Trimethylsilylacetylene (4.1 mL, 28.8 mmol) and tetrakis(triphenylphosphine)palladium (0) (832 mg, 0.72 mmol) were added to a suspension of (1) (4.06 g, 14.4 mmol) and copper (I) iodide (274 mg, 1.44 mmol) in triethylamine (120 mL) that had been deoxygenated with argon. The mixture was deoxygenated with argon and then stirred under argon at room temperature for 40 hours. Aqueous hydrochloric acid (3 M, 320 mL) and dichloromethane (250 mL) were added. The organic layer was separated and the aqueous layer was extracted with dichloromethane (3×50 mL). The combined organic layers were washed with aqueous hydrochloric acid (3 M, 30 mL), water (250 mL), brine (250 mL), dried over anhydrous magnesium sulfate, filtered and then the solvent was completely removed. The residue was purified by column chromatography over silica using a dichloromethane/light petroleum mixture (1:4) as the eluent. The main band was isolated and the solvent completely removed to give (2) (2.59 g, 72%).

Preparative Example 3

2-(4-Ethynylphenyl)pyridine (3)

A solution of (2) (2.26 g, 8.97 mmol) and tetrabutylammonium fluoride (1 M in tetrahydrofuran, 36 mL, 36 mmol) in tetrahydrofuran was stirred at room temperature under argon for 3 hours. Dichloromethane (100 mL) and water (150 mL) were added. The organic layer was separated and the aqueous layer was extracted with dichloromethane (3×15 mL). The combined organic layers were washed with brine (200 mL), dried over anhydrous magnesium sulfate, filtered and the solvent completely removed. The residue was purified by passing through a silica plug using dichloromethane as eluent to give (3) (1.44 g, 90%).

Preparative Example 4

2-[4-(2,3,4,5-tetraphenylphenyl)phenyl]pyridine (5)

A solution of 2,3,4,5-tetraphenylcyclopentadienone (4) (Morgenroth et al, *Tetrahedron* 1997, 53, 15349) (1.14 g, 2.96 mmol) and (3) (354 mg, 1.98 mmol) in diphenyl ether (3 mL) was deoxygenated and heated at 210° C. under argon for 3 hours. The reaction mixture was purified by column chromatography over silica using a dichloromethane/light petroleum mixture (1:1) as eluent to give (5) (988 mg, 93%).

Example 1

Fac-tris[2-{4-[(2,3,4,5-tetraphenyl)phenyl]phenyl}-pyridinato-N,$C^{2'}$]iridium(III) (6)

A mixture of (5) (1.00 g, 1.87 mmol), iridium trichloride trihydrate (263 mg, 0.747 mmol), water (8 mL) and 2-ethoxyethanol (25 mL) was deoxygenated and then heated at reflux with stirring under argon for 16 hours. The reaction mixture was filtered and the residue was washed with water (3×50 mL). The residue was collected and dissolved in dichloromethane (200 mL), washed with water (3×100 mL), brine (100 mL), dried over anhydrous magnesium sulfate, filtered and then the solvent was completely removed to leave a yellow solid (1.19 g) containing a mixture of bis-iridium bis-chloro dimer and unreacted (5). The mixture, (5) (1.32 g, 2.46 mmol) and silver trifluoromethylsulfonate (190 mg, 0.74 mmol) in diglyme (4 mL) was heated at 130° C. under argon for 2 days. The diglyme was removed and the crude product was purified by column chromatography over silica using a dichloromethane/light petroleum mixture (1:1) as eluent. The main band was collected and the solvent completely removed to give a bright yellow solid (1.05 g). Recrystallisation from a dichloromethane/methanol mixture gave (6) (841 mg, 63%).

Preparative Example 5

9,9-Di-n-propyl-2-bromofluorene (7)

50% Aqueous sodium hydroxide (500 mL) was added to a solution of 2-bromofluorene (52.8 g, 215 mmol) and tetrabutylammonium bromide (3.47 g, 10.8 mmol) in toluene (500 mL), and heated to 50° C. After 90 minutes 1-bromopropane (60 mL, 650 mmol) was added, and the solution stirred at 50° C. for 16 hours. The organic layer was separated, washed with water (2×500 mL), brine (500 mL), dried over magnesium sulfate, and the solvent removed. Recrystallisation from a dichloromethane/methanol mixture gave (7) (51.5 g, 73%).

Preparative Example 6

9,9-Di-n-propylfluorenyl-2-boronic acid (8)

Tert-butyl lithium (87 mL, 1 M solution in pentane, 150 mmol) was added to a solution of (7) (44.4 g, 135 mmol) in tetrahydrofuran (600 mL) which had been cooled in a dry ice/acetone bath. After 1 hour trimethylborate (77 mL, 680 mmol) was added, and the solution stirred for 16 hours gradually warming to room temperature. Aqueous hydrochloric acid (3 M, 80 mL) was added, and the solution stirred for 2 hours. The layers were separated, and the aqueous layer was extracted with diethyl ether (3×20 mL). The combined organic extracts were washed with brine (500 mL), dried over magnesium sulfate and the solvent was removed. Purification by silica plug (using light petroleum then diethyl ether as the eluent) gave (8) (24.3 g, 61%).

Preparative Example 7

2,5-Diphenyl-3,4-di(4-bromophenyl)cyclopentadienone (9)

A solution of potassium hydroxide (1.60 g, 29 mmol) in ethanol (30 mL) was added to a warmed (75° C.) solution of diphenylacetone (12.0 g, 57 mmol) and 4,4'-dibromobenzil (21.0 g, 57 mmol) in ethanol (130 mL). The resulting dark brown solution was poured into methanol, and the dark precipitate filtered to give (9) (26.0 g, 84%).

Preparative Example 8

2,5-diphenyl-3,4-di{4-[9,9-di-n-propyl-2-fluorenyl]phenyl}cyclopentadienone (10)

Tetrakis(triphenylphosphine)-palladium (0) (1.48 g, 1.3 mmol) was added to a solution of (9) (13.8 g, 26 mmol) and (8) (22.6 g, 77 mmol) in a mixture of ethanol (100 mL), 2M aqueous sodium carbonate (100 mL) and toluene (300 mL) that had been deoxygenated with argon. The solution was deoxygenated and heated at reflux for 16 hours, then poured into methanol. The resulting brown precipitate was filtered, dissolved in chloroform, washed with brine, and dried over magnesium sulfate. The solution was poured into methanol, and the brown precipitate filtered to give (10) (22.4 g, 99%).

Preparative Example 9

2-{4-[2,5-Diphenyl-3,4-di(4-{9,9-di-n-propyl-2-fluorenyl}phenyl)phenyl]phenyl}pyridine (11)

A solution of (10) (1.48 g, 1.67 mmol) and (3) (200 mg, 1.12 mmol) in diphenyl ether (3 mL) was deoxygenated and heated at 210° C. under argon for 3 hours. The crude product was purified by column chromatography over silica using dichloromethane: light petroleum (1:1) as the eluent. The main band was isolated and the solvent completely removed to give (11) (1.09 g, 95%).

Example 2

Fac-tris[2-{4-[2,5-d]phenyl-3,4-di(4-[9,9-di-n-propyl-2-fluorenyl]phenyl)phenyl]phenyl}pyridinato-N,C$^{2'}$]iridium(III) (12)

A mixture of (11) (1.50 g, 1.45 mmol), iridium trichloride trihydrate (205 mg, 0.58 mmol), water (10 mL) and 2-ethoxyethanol (30 mL) was deoxygenated, then stirred and heated at reflux under argon for 16 hours. The yellow precipitate was filtered, washed with water and dried to leave a yellow solid (1.48 g) containing a mixture of bis-iridium bis-chloro dimer and unreacted ligand (11). The mixture, (11) (3.18 g, 3.0 mmol) and silver trifluoromethanesulfonate (149 mg, 0.58 mmol) in diglyme (20 mL) was heated at 130° C. for 3 days. The diglyme was removed and the crude product was purified by column chromatography over silica using dichloromethane: light petroleum (1:1) as the eluent. The main band was isolated and the solvent completely removed to give (12) (620 mg, 32%).

Example 3

Fac-tris[2-{5-[2,5-d]phenyl-3,4-di(4-[9,9-di-n-propyl-2-fluorenyl]phenyl)phenyl]phenyl}pyridinato-N,C$^{2'}$]iridium(III)

Synthesis as Example 2, but substituting 2-(3-ethynylphenyl)pyridine (Preparative Example 17) instead of 2-(4-ethynylphenyl)pyridine (Preparative Example 9).

Example 4

Fac-tris[2-{5-[2,5-d]phenyl-3,4-di(4-[2-ethylhexyloxyphenyl]phenyl)phenyl]phenyl}pyridinato-N,C$^{2'}$]iridium(II)

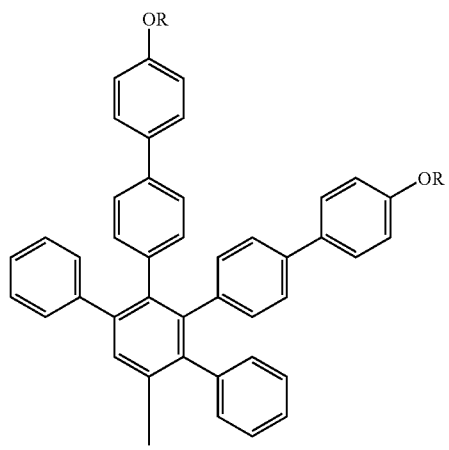

-continued
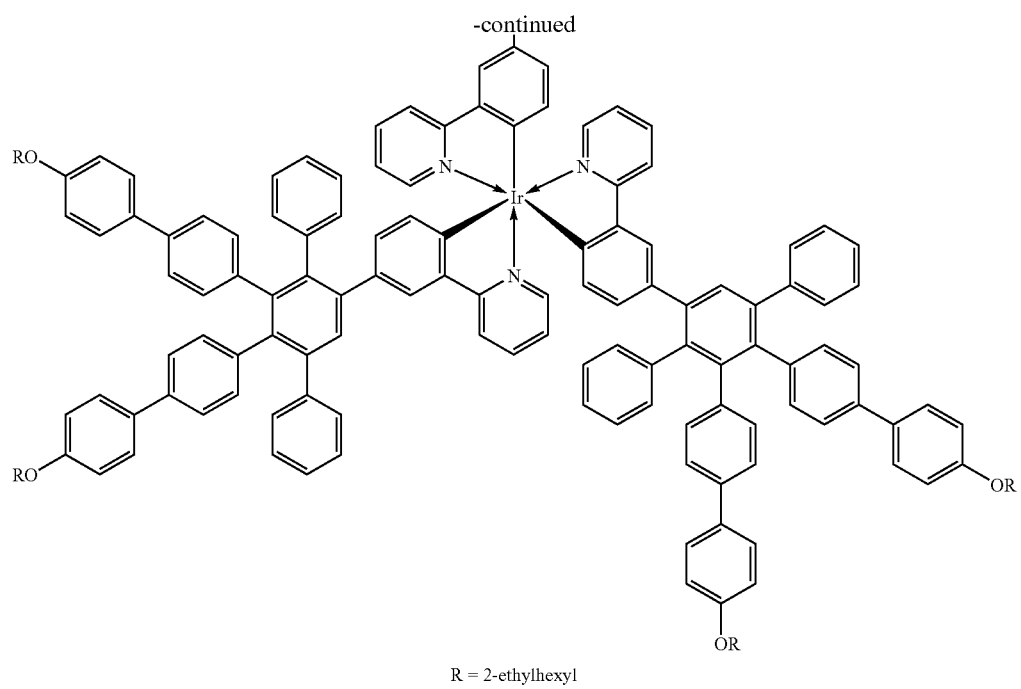
R = 2-ethylhexyl
Synthesis as for Example 3, but substituting 4-(2-ethylhexyloxy)phenylboronic acid instead of 9,9-di-n-propylfluorenyl-2-boronic acid (8) in Preparative Example 8.
Example 5
Fac-tris[2-{5-[(2,3,4,5-tetraphenyl)phenyl]phenyl}pyridinato-N,$C^{2'}$]iridium(III)
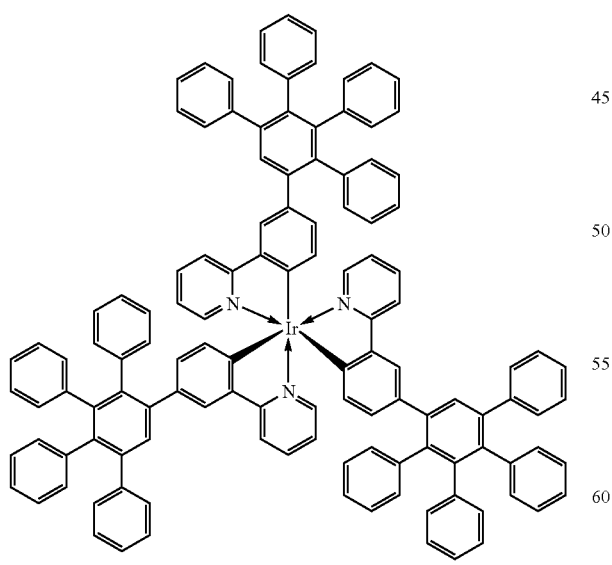
Synthesis as for Example 1, but substituting 1,3-diiodobenzene instead of 1,4-diiodobenzene in Preparative Example 1.

Example 6
Fac-tris{2-phenyl-5-[2,5-d]phenyl-3,4-di(4-[9,9-di-n-propyl-2-fluorenyl]-phenyl)phenyl]pyridinato-N,C$^{2'}$}iridium(III)
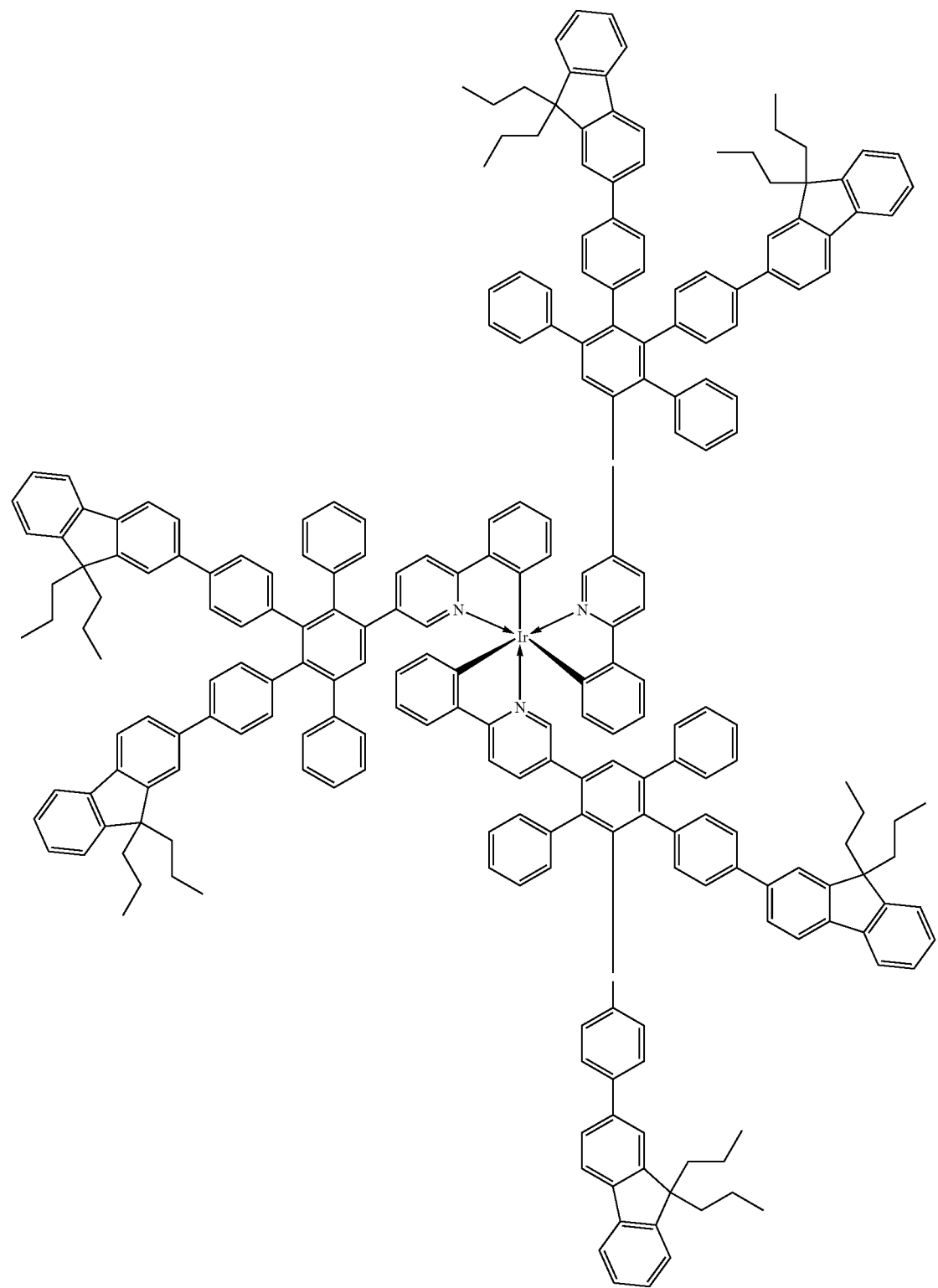

The dendrimer of Example 6 was prepared by analogous procedures to that given for the preparation of Example 2, except that in Example 6 the dendron is bound to the pyridyl ring of phenylpyridine moiety rather than to the phenyl ring.

yield is no lower than those obtained from the complexation of ligands dendronised only on the phenyl ring, showing that the presence of the bulky dendron on the pyridine ring does not inhibit complexation.

Scheme 1:

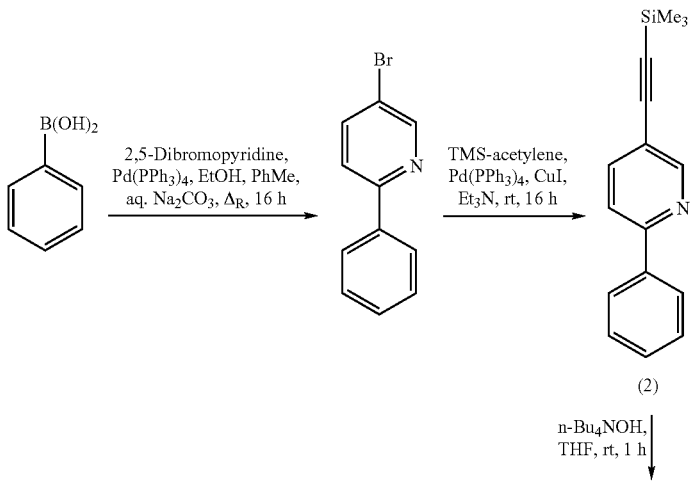

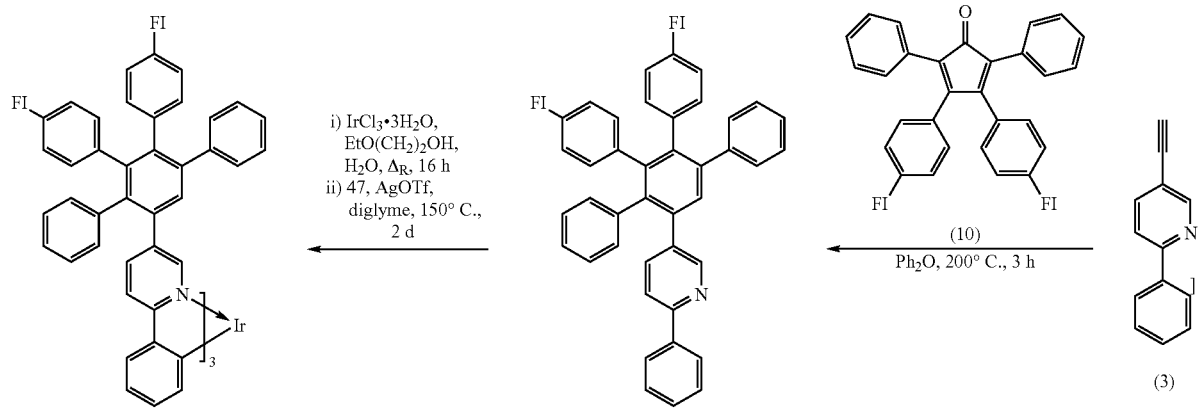

To explain the synthesis in more detail, the Suzuki reaction between phenylboronic acid and 2,5-dibromopyridine gave 2-phenyl-5-bromopyridine in an 86% yield (see scheme 1 above). The reaction occurred preferentially on the 2 position on the pyridine ring, which is activated by the adjacent nitrogen. Reaction of 2-phenyl-5-bromopyridine with trimethylsilylacetylene under Sonogashira conditions gave the 2-phenyl-5-(trimethylsilylethynyl)pyridine (2) in an 88% yield, which could be deprotected to 2-phenyl-5-ethynylpyridine (3) in a yield of 93% using tetra-n-butylammonium hydroxide. The Diels-Alder reaction between (3) and the difluorenylcyclopentadienone (10) gave the dendronised ligand in a 48% yield, after purification by precipitation of the ligand from a dichloromethane solution by pouring the solution into ethanol. The complex was formed by the two-step procedure via the bis(chloro)-bis(iridium) dimer in a yield of 50%. This Preparative Example 10

1,3-Di(4-bromophenyl)acetone (13)

A solution of 4-bromophenylacetic acid (25.44 g, 118 mmol) in dichloromethane (200 cm$^3$) was added over 1 hour to a solution of N,N'-dicyclohexylcarbodiimide (26.85 g, 130 mmol) and 4-dimethylaminopyridine (3.60 g, 30 mmol) in dichloromethane (150 cm$^3$), and the reaction was stirred at room temperature for 20 hours. The white precipitate was filtered, and washed with dichloromethane. The solvent was removed from the filtrate to give an orange solid. The crude product was purified by column chromatography over silica using chloroform: light petroleum (3:1) as eluent, then recrystallisation from ethanol, to give (13) as a white crystalline solid (10.23 g, 47%).

Preparative Example 11

2,3,4,5-Tetra(4-bromophenyl)cyclopentadienone (14)

A solution of potassium hydroxide (230 mg, 4.1 mmol) in ethanol (5 cm$^3$) was added to a solution of (13) (3.01 g, 8.2 mmol) and 4,4'-dibromobenzil (3.01 g, 8.2 mmol) in ethanol (45 cm$^3$) at 70° C., and the reaction was stirred at 70° C. for 4 hours. Water (200 cm$^3$) and dichloromethane (200 cm$^3$) were added, and the layers were separated. The organic layer was washed with brine (200 cm$^3$) and dried over magnesium sulfate. The solvent was removed to leave a dark purple solid. The crude product was passed through a plug of silica, and then recrystallised from a dichloromethane/ethanol mixture to give (14) as a dark purple crystalline solid (3.87 g, 68%).

Preparative Example 12

2-(3-Iodophenyl)pyridine (15)

n-Butyllithium (2.0 M in cyclohexane, 8 cm$^3$) was added dropwise to a solution of 1,3-diiodobenzene (5.19 g, 16 mmol) in ether (50 cm$^3$), cooled in a salt-ice bath, and the solution was stirred for 10 minutes. 2-Fluoropyridine (1.4 cm$^3$, 16 mmol) was added, at which the pale yellow cloudy solution turned dark brown, and the reaction was allowed to warm to room temperature over 1 hour. Water (50 cm$^3$) and ether (20 cm$^3$) were added, and the layers were separated. The aqueous layer was extracted with ether (3×50 cm$^3$). The combined organic extracts were washed with brine (150 cm$^3$), and dried over magnesium sulfate. The solvent was removed to leave a brown oil. Purification of the crude product by column chromatography over silica using dichloromethane: light petroleum (1:1) as eluent gave (15) as an orange oil (1.04 g, 24%).

Preparative Example 13

2-(3-(Trimethylsilylethynyl)phenyl)pyridine (16)

A mixture of (15) (128 mg, 0.46 mmol), copper(I) iodide (9 mg, 50 µmol) and triethylamine (10 cm$^3$) was deoxygenated with argon. Tetrakis(triphenylphosphine)palladium(0) (26 mg, 23 µmol) was added, and the mixture was deoxygenated with argon again. Trimethylsilylacetylene (0.15 cm$^3$, 1 mmol) was added, and the reaction was stirred at room temperature for 9 hours. Water (50 cm$^3$), aqueous hydrochloric acid (3 M, 5 cm$^3$) and dichloromethane (50 cm$^3$) were added, and the layers were separated. The organic layer was washed with brine (50 cm$^3$) and dried over magnesium sulfate, and the solvent was removed to leave a black solid. The crude product was purified by column chromatography using dichloromethane: light petroleum 3:2 as eluent, to give (16) as a pale brown oil (110 mg, 96%).

Preparative Example 14

2-(3-Ethynylphenyl)pyridine (17)

Tetra-n-butylammonium hydroxide (22 cm$^3$, 1 M in methanol) was added to a solution of (16) (1.87 g, 7.4 mmol) in tetrahydrofuran (20 cm$^3$), and the solution was stirred at room temperature for 1 hour. Dichloromethane (20 cm$^3$) and water (50 cm$^3$) were added, and the layers were separated. The aqueous layer was extracted with dichloromethane (3×10 cm$^3$). The combined organic extracts were washed with brine (50 cm$^3$) and dried over magnesium sulfate, and the solvent was removed to leave an orange oil. The crude product was passed through a silica plug using dichloromethane: light petroleum (1:1) as eluent, and the solvent was completely removed to give (17) as a colourless oil (1.31 g, 99%).

Preparative Example 15

2-{3-[2,3,4,5-tetra(4-bromophenyl)phenyl]phenyl}pyridine (18)

A solution of (14) (1.19 g, 1.7 mmol) and (17) (253 mg, 1.4 mmol) in diphenyl ether (20 cm$^3$) was deoxygenated with argon and heated to 200° C. for 3 hours. The crude product was purified by column chromatography over silica using dichloromethane: light petroleum (1:1) as eluent. The main band was isolated and the solvent completely removed to give (18) as a white solid (1.18 g, 99%).

Preparative Example 16

2-{3-[2,3,4,5-Tetra(4-{9,9-di-n-propyl-2-fluorenyl}phenyl)phenyl]phenyl}pyridine (19)

A solution of (18) (905 mg, 1.1 mmol) and (8) (2.50 g, 8.5 mmol) in a mixture of toluene (50 cm$^3$), ethanol (15 cm$^3$) and aqueous sodium carbonate (2 M, 15 cm$^3$) was deoxygenated with argon. Tetrakis(triphenylphosphine)palladium(0) (245 mg, 0.21 mmol) was added, and the mixture was deoxygenated with argon again, then heated at reflux for 20 hours. Water (200 cm$^3$) and dichloromethane (200 cm$^3$) were added, and the layers were separated. The aqueous layer was extracted with dichloromethane (3×10 cm$^3$). The combined organic extracts were washed with brine (250 cm$^3$) and dried over magnesium sulfate, and the solvent was removed to leave a black solid. The crude product was purified by column chromatography using dichloromethane: light petroleum (1:2) as eluent, to give (19) as a pale yellow solid (1.53 g, 94%).

Example 7

Fac-tris[2-{5-[2,3,4,5-tetra(4-[9,9-di-n-propyl-2-fluorenyl]phenyl)phenyl]phenyl}pyridinato-N,C²']iridium(III) (20)

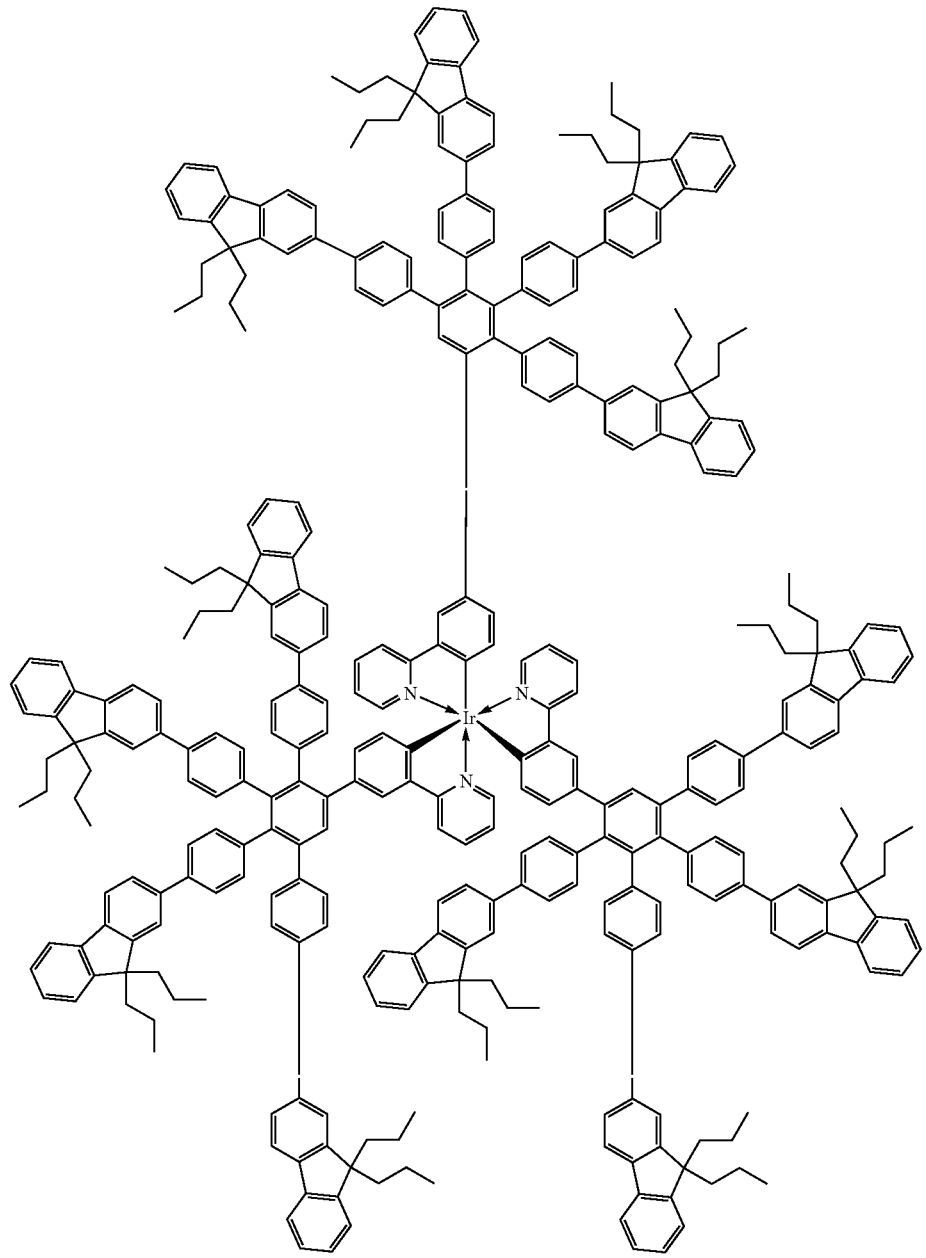

A mixture of (19) (325 mg, 0.21 mmol), iridium(III) trichloride trihydrate (30 mg, 85 μmol), water (1.5 cm³) and 2-ethoxyethanol (4.5 cm³) was deoxygenated with argon, and heated to reflux for 16 hours. Water (30 cm³) and dichloromethane (30 cm³) were added, and the layers were separated. The aqueous layer was extracted with dichloromethane (3×5 cm³). The combined organic extracts were washed with brine (50 cm³) and dried over magnesium sulfate, and the solvent was removed to leave a yellow solid. A solution of this material, further (19) (570 mg, 0.37 mmol) and silver trifluoromethanesulfonate (22 mg, 85 μmol) in diglyme (2 cm³) was deoxygenated with argon, and heated to 150° C. for 16 hours. Water (20 cm³) and dichloromethane (20 cm³) were added, and the layers were separated. The aqueous layer was extracted with dichloromethane (3×5 cm³). The combined organic extracts were washed with brine (50 cm³) and dried over magnesium sulfate, and the solvent was removed to leave a brown solid. The crude product was purified by column chromatography over silica using dichloromethane:light petroleum (1:3) as eluent, to give (20) as a bright yellow solid (180 mg, 44%).

Example 8
Fac-tris[2-{4-[2,3,4,5-tetra(4-[9,9-di-n-propyl-2-fluorenyl]phenyl)phenyl]phenyl}pyridinato-N,C²']iridium(III)
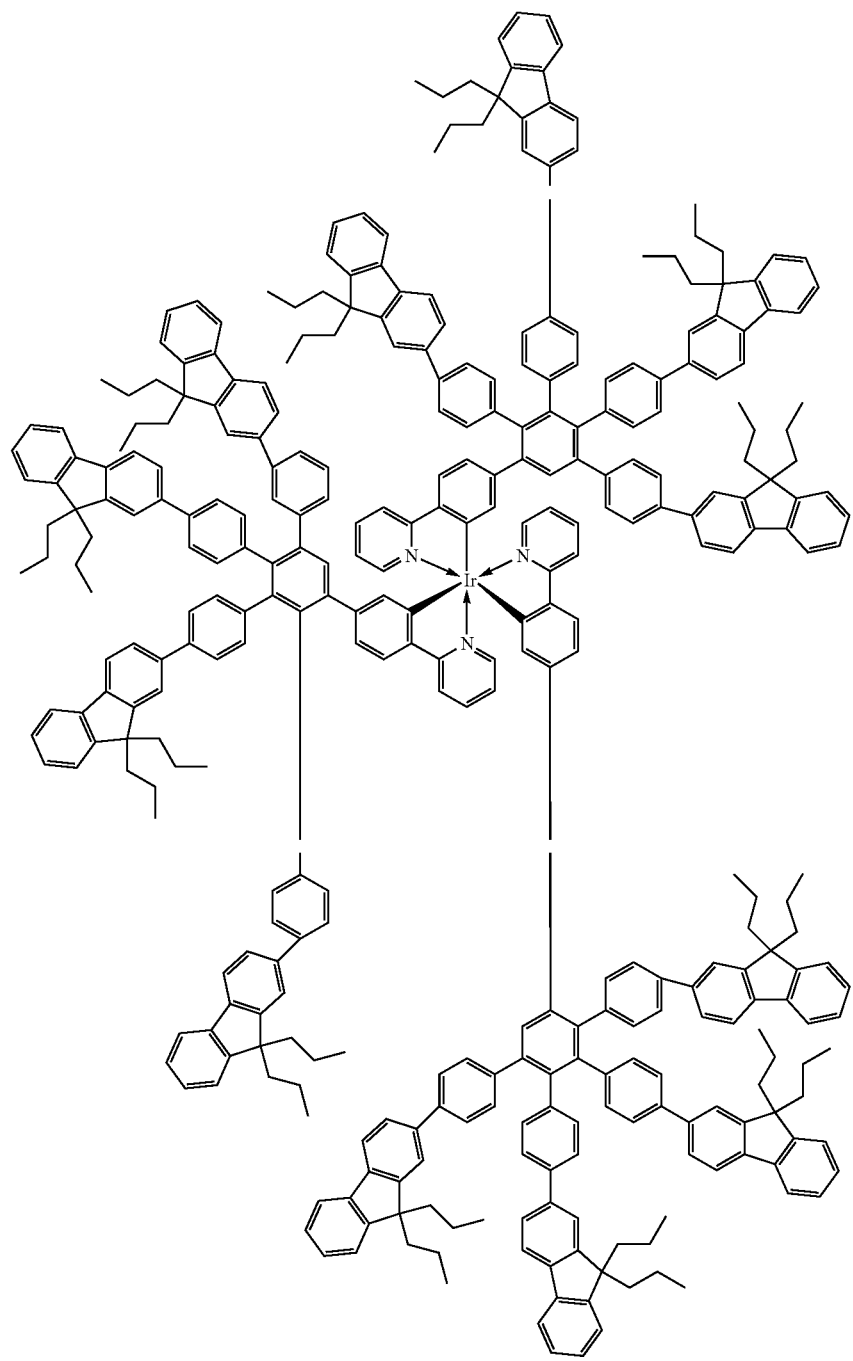

Synthesis as for Example 7, but substituting 2-(4-ethynylphenyl)pyridine (3) for 2-(3-ethynylphenyl)pyridine (17) in Preparative example 15.

Preparative Example 17

1-Bromo-3-(trimethylsilyl)benzene (21)

n-Butyllithium (38 cm$^3$, 1.6 M in hexanes) was added dropwise to a solution of 1,3-dibromobenzene (5.1 cm$^3$, 42 mmol) in ether (200 cm$^3$) cooled in a dry ice/acetone bath, and the reaction was stirred for 1 hour. A solution of trimethylsilylchloride (21 cm$^3$, 170 mmol) in ether (20 cm$^3$) was added, and the reaction was stirred for 20 hours, gradually warming to room temperature. Water (200 cm$^3$) was added, and the layers were separated. The aqueous layer was extracted with ether (3×50 cm$^3$). The combined organic extracts were washed with brine (300 cm$^3$) and dried over magnesium sulfate, and the solvent was removed to leave a colourless oil. The crude product was passed through a plug of silica using 30-40 light petroleum as the eluent, to give (21) as a colourless oil (9.65 g, 99%).

Preparative Example 18

3-(Trimethylsilyl)phenylboronic acid (22)

t-Butyllithium (28 cm$^3$, 1.7 M in pentane) was added to a solution of (21) (9.65 g, 42 mmol) in ether (200 cm$^3$) cooled in a dry ice/acetone bath, and the reaction was stirred for 30 minutes. Trimethyl borate (20 cm$^3$, 170 mmol) was added, and the reaction was stirred for 16 hours, gradually warming to room temperature. Aqueous hydrochloric acid (3 M, 20 cm$^3$) was added, and the reaction was stirred for a further 2 hours. Water (200 cm$^3$) was added, and the layers were separated. The aqueous layer was extracted with ether (3×30 cm$^3$). The combined organic extracts were washed with brine (300 cm$^3$) and dried over magnesium sulfate, and the solvent was removed to leave a white solid. The crude product was passed through a plug of silica using light petroleum then ether as the eluent. The ether band was collected, and the solvent was removed to leave (22) as a brown solid (7.04 g, 86%).

Preparative Example 19

2,5-Di(3-(trimethylsilyl)phenyl)pyridine (23)

A solution of (22) (5.70 g, 29.4 mmol) and 2,5-dibromopyridine (2.32 g, 9.8 mmol) in a mixture of toluene (120 cm$^3$), ethanol (40 cm$^3$) and aqueous sodium carbonate (2 M, 40 cm$^3$) was deoxygenated with argon. Tetrakis(triphenylphosphine)palladium(0) (566 mg, 0.49 mmol) was added, and the solution was deoxygenated with argon again, then heated at reflux for 16 hours. Water (200 cm$^3$) and dichloromethane (200 cm$^3$) were added, and the layers were separated. The aqueous layer was extracted with dichloromethane (3×50 cm$^3$). The combined organic extracts were washed with brine (500 cm$^3$) and dried over magnesium sulfate, and the solvent was removed to leave a black oil. The crude product was purified by column chromatography using dichloromethane: light petroleum (1:1) as eluent, to give (23) as a white solid (3.48 g, 94%).

Preparative Example 20

2,5-Di(3-iodophenyl)pyridine (24)

A solution of iodine monochloride (26 cm$^3$, 1 M in dichloromethane) was diluted with 25 cm$^3$ of dichloromethane (25 cm$^3$), and added dropwise to a solution of (23) (1.97 g, 5.2 mmol) in dichloromethane (125 cm$^3$) at 0° C., and the solution was stirred at 0° C. under argon for 2 hours. Water (150 cm$^3$) was added. Sodium thiosulfate was added until the solution turned from purple to colourless. The layers were separated, and the aqueous layer was extracted with dichloromethane (3×10 cm$^3$). The combined organic extracts were washed with brine (200 cm$^3$), dried over magnesium sulfate, and the solvent was removed. The crude product was passed through a plug of silica using dichloromethane: light petroleum (1:1) as eluent, to give (24) as a white solid (2.20 g, 87%).

Preparative Example 21

Fac-tris{2-[5-trimethylsilylethynylphenyl]-5-[3-trimethylsilylethynylphenyl]pyridinato-N,C$^{2'}$}iridium (III) (25)

A mixture of (24) (143 mg, 0.30 mmol), iridium trichloride trihydrate (42 mg, 0.12 mmol), water (1.5 cm$^3$) and 2-ethoxyethanol (4.5 cm$^3$) was deoxygenated with argon, then heated to reflux for 16 hours. Water (50 cm$^3$) and dichloromethane (50 cm$^3$) were added, and the layers were separated. The aqueous layer was extracted with dichloromethane (3×5 cm$^3$). The combined organic extracts were washed with brine (50 cm$^3$) and dried over magnesium sulfate. The solvent was removed to leave a brown solid. This was passed through a silica plug using dichloromethane: light petroleum (1:1) as eluent, to give and orange solid. The solid was heated at 150° C. under argon for 16 hours with further (24) (223 mg, 0.46 mmol) and silver trifluoromethanesulfonate (31 mg, 0.12 mmol) in diglyme (2 cm$^3$). Water (50 cm$^3$) and dichloromethane (50 cm$^3$) were added, and the layers were separated. The aqueous layer was extracted with dichloromethane (3×5 cm$^3$). The combined organic extracts were washed with brine (60 cm$^3$) and dried over magnesium sulfate. The solvent was removed to leave a brown solid. The crude product was purified by column chromatography over silica using dichloromethane: light petroleum (1:1) as eluent. The orange band was isolated and the solvent was completely removed to give an orange solid containing a mixture of fac-tris{2-[5-iodophenyl]-5-[3-iodophenyl]pyridinato-N,C$^{2'}$}iridium(III) and complexes containing 5 and 4 iodine substituents. The mixture of iodinated complexes (111 mg, 68 µmol), copper(I) iodide (8 mg, 40 µmol) and triethylamine (4 cm$^3$) was degassed. Tetrakis(triphenylphosphine)palladium(0) (23 mg, 20 µmol) was added, and the mixture was degassed again. Trimethylsilylacetylene (0.3 cm$^3$, 2.1 mmol) was added, and the mixture was stirred under argon at room temperature for 16 hours. Water (50 cm$^3$) and dichloromethane (50 cm$^3$) were added, and the layers were separated. The aqueous layer was extracted with dichloromethane (3×5 cm$^3$). The combined organic extracts were washed with brine (50 cm$^3$) and dried over magnesium sulfate. The solvent was removed to leave a brown solid. The crude product was purified by column chromatography over silica using dichloromethane: light petroleum (1:3) as eluent. The first yellow band was isolated and the solvent completely removed to leave (25) as an orange solid (82 mg, 47%).

Example 9
Fac-tris[2-{5-[2,5-diphenyl-3,4-di(4-[9,9-di-n-propyl-2-fluorenyl]phenyl)phenyl]phenyl}-5-{3-(2,5-diphenyl-3,4-di(4-[9,9-di-n-propyl-2-fluorenyl]phenyl)phenyl)phenyl}pyridinato-N,C$^{2'}$]iridium(III) (26)
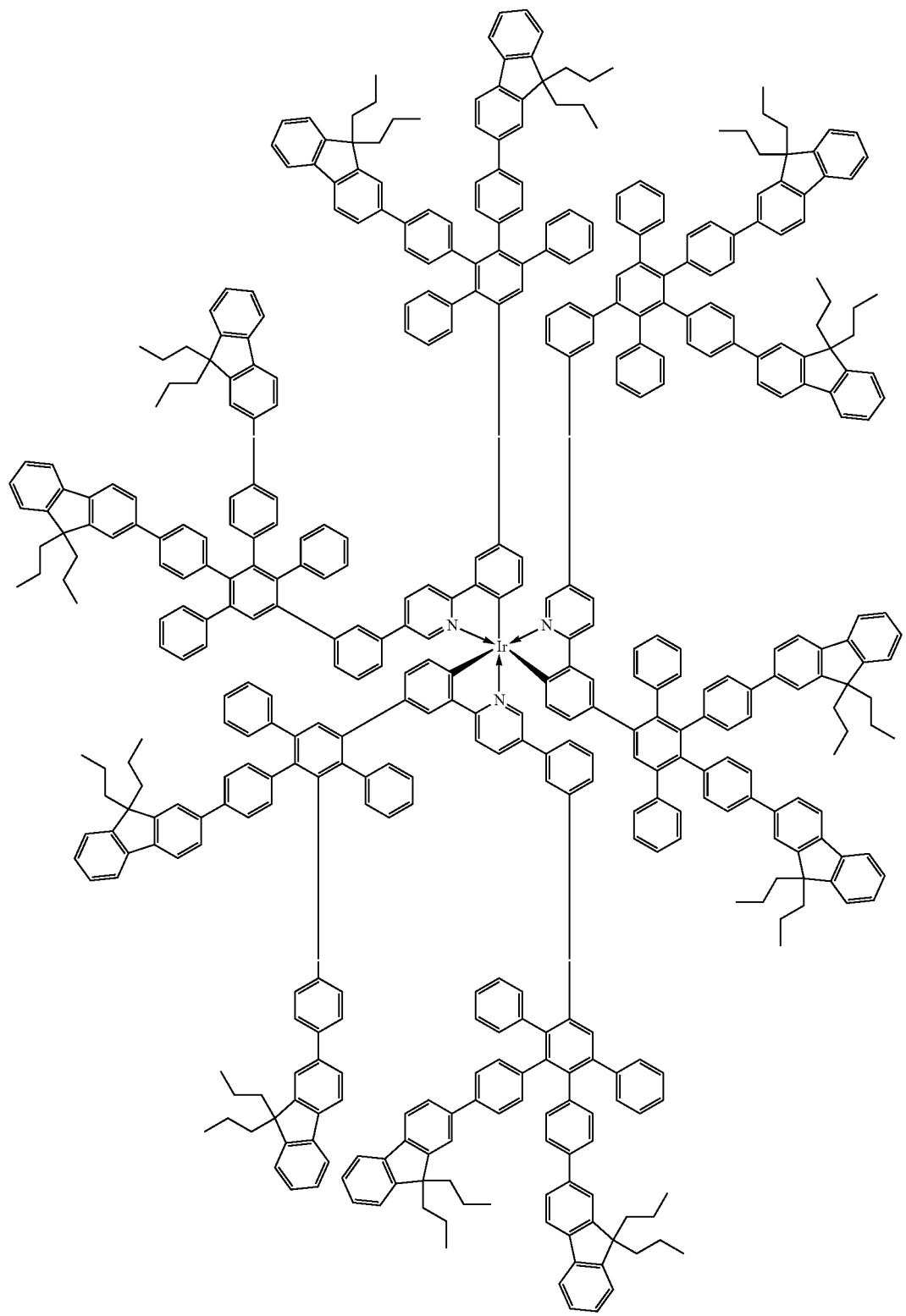

Tetra-n-butylammonium fluoride (1.0 cm³, 1 M in tetrahydrofuran) was added to a solution of (25) (75 mg, 51 μmol) in tetrahydrofuran (10 cm³), and the reaction was stirred at room temperature for 3 hours. Water (30 cm³) and dichloromethane (30 cm³) were added, and the layers were separated. The aqueous layer was extracted with dichloromethane (3×5 cm³). The combined organic extracts were washed with brine (50 cm³) and dried over magnesium sulfate, and the solvent was removed to leave and orange solid (57 mg). A solution of this material and (10) (450 mg, 0.51 mmol) in diphenyl ether (3 cm³) was deoxygenated with argon, and heated to 180° C. for 2 hours. The crude product was purified by column chromatography using dichloromethane: light petroleum (1:3) as eluent, to give (26) as an orange solid (123 mg, 39%).

Example 10

Fac-tris[2-{4-[2,5-diphenyl-3,4-di(4-[2-ethylhexyloxyphenyl]phenyl)phenyl]phenyl}-pyridinato-N, C²']iridium(III)

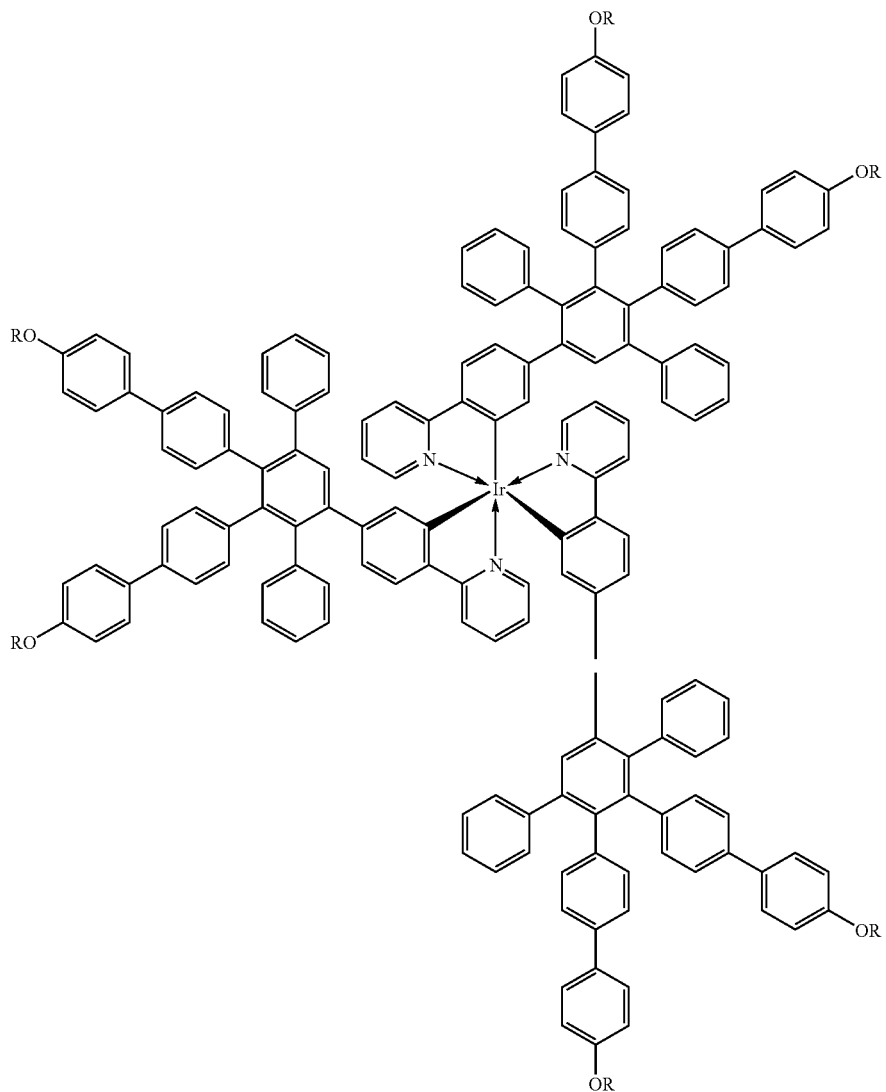

R = 2-ethylhexyl

Synthesis as Example 1, but substituting 2,3,4,5-tetraphenylcyclopentadienone (4) with the 4-(2-ethylhexyloxyphenyl) derivative as in example 4.

Example 11

PLQY Testing

Solution photoluminescence quantum yields (PLQYs) for the dendrimers of Examples 1 to 5 and 7 to 9 were measured by a relative method using quinine sulfate in 0.5 M sulfuric acid which has a photoluminescence quantum yield of 0.546, as the standard. The dendrimers were dissolved in toluene and freeze-thaw degassed. Photoluminescence spectra were recorded in a JY Horiba Fluoromax 2 fluorimeter, with the dendrimer solutions excited at 360 nm. The optical densities of the standard and sample were similar and small (less than/equal to 0.1).

Neat films were spin-coated from chloroform solutions with a dendrimer concentration of around 10 mg/mL at 800-1200 rpm for 1 min to give a thickness of about 50-60 nm. Blend films were spincoated from solutions of total solute concentration of 20 mg/mL at 800 r.p.m. for 1 min to give films of thickness approximately 150 nm. The PLQY of the films was measured using an integrating sphere in accordance with Greenham et al, *Chem. Phys. Lett.* 1995, 241, 89, using a Helium Cadmium laser (Kimmon) as the excitation source. The excitation power was 0.2 mW at 325 nm and the sphere was purged with nitrogen. The accuracy of these measurements is estimated to be ±10% of the stated value.

The results of the testing are shown in Table 1 below.

TABLE 1

| Example No. | Solution PLQY | Film |
| --- | --- | --- |
| 1 | 69% | 50% |
| 2 | 70% | 40% |
| 3 | 75% | 25% |
| 4 | 80% | 75% |
| 5 | 92% | 14% |
| 6 | 70% | 25% |
| 7 | 56% | 25% |
| 8 | 65% | 25% |
| 9 | 75% | 37% |
| 10 | 70% | 25% |

Example 12

Device Testing

Bilayer blend devices (20:80 wt % in CBP) were prepared in accordance with the general device description described earlier. The device structure used was:

ITO/Dendrimer blend/TPBI/LiF/Al

TPBI is the electron transporting/hole blocking material 1,3,5-tris(2-N-phenylbenzimidazolyl)benzene. The results at 100 cd/m² are shown in Table 2 below.

TABLE 2

| Example No. | Drive Voltage | Power Efficiency | EQE (cd/A) |
| --- | --- | --- | --- |
| 1 | 4.3 V | 27 lm/W | 10% (37.5) |
| 2 | 6.4 V | 17 lm/W | 9.5% (35.5) |
| 3 | 7.2 V | 2 lm/W | 1.4% (4.7) |
| 4 | 8.4 V | 2.3 lm/W | 1.9% (6.2) |
| 5 | 5.6 V | 22.4 lm/W | 11% (39.6) |
| 6 | 13.2 V | 7.2 lm/W | 8.6% (30.2) |
| 7 | 9.6 V | 12.6 lm/W | 11.1% (38.4) |
| 8 | 14.4 V | 2.9 lm/W | 3.7% (13.2) |

The invention claimed is:

1. A dendrimer of formula (I):

$$[DENDRON^1]_x\text{-CORE}[B\text{-}[X]_b]_a \qquad (I)$$

wherein:
CORE is:
(a) a group containing a metal ion, which group comprises a metal cation and attached ligands, wherein the attached ligands form part of the CORE and include a bidentate ligand, which bidentate ligand comprises a carbocyclic ring which acts as a carbon donor and a heterocyclic ring which acts as a heteroatom donor, wherein the carbocyclic ring and the heterocyclic ring are directly linked to each other by a single bond, wherein the carbocyclic ring is a phenyl group, and the heterocyclic ring is a heteroaryl group which is a 5- or 6-membered aromatic ring containing at least one heteroatom, and wherein at least one dendron of said formula B-[X]$_b$ is bound to said bidentate ligand, provided that the carbocyclic ring which is a phenyl group and the heterocyclic ring which is a heteroaryl group are otherwise unsubstituted, and provided that when at least one dendron of formula B-[X]$_b$ is bound to the carbocyclic ring, each dendron is bound to a meta- or para-position of the ring relative to the bond between the ring and the metal, and provided that when at least one dendron of formula B-[X]$_b$ is bound to the heterocyclic ring and the heterocyclic ring is a six-membered ring, each dendron is bound to a meta- or para-position of the ring relative to the bond between the ring and the metal, or (b) a non-metallic core which is a non-polymeric organic group;

B is a phenyl ring;
a is an integer of from 3 to 8;
b is an integer of from 3 to 5;
x is zero or an integer of from 1 to 7;
each X is the same or different and represents an aryl or heteroaryl ring, or represents an at least partially conjugated dendritic molecular structure comprising at least one branching group and optionally at least one linking group, the branching groups being selected from the group consisting of aryl and heteroaryl groups and nitrogen atoms, and the linking groups being selected from the group consisting of aryl, heteroaryl, vinyl and acetylenyl groups, said branching groups being bonded to three or more groups, and said linking groups being bonded to two groups, said dendritic molecular structure terminating at its distal points in aryl and/or heteroaryl groups;

DENDRON$^1$ represents an at least partially conjugated dendritic molecular structure comprising at least one branching group and optionally at least one linking group, the branching groups being selected from the group consisting of aryl and heteroaryl groups and nitrogen atoms, and the linking groups being selected from the group consisting of aryl, heteroaryl, alkyleneoxy, vinyl and acetylenyl groups, said branching groups being bonded to three or more groups, and said linking groups being bonded to two groups, said dendritic molecular structure terminating at its distal points in aryl and/or heteroaryl groups; and wherein the dendrimer further comprises one or more surface groups selected from the group consisting of hydroxy; $C_{1-15}$ alkyl; $C_{2-15}$ alkenyl; amine; $C_{1-15}$ alkylamine; di($C_{1-15}$) alkylamine; COOR wherein R is hydrogen or $C_{1-15}$ alkyl; $C_{1-15}$ alkoxy; $C_{2-15}$ alkenyloxy; $C_{6-10}$ aryloxy; $O_2SR$ wherein R is $C_{1-15}$ alkyl or $C_{2-15}$ alkenyl; $SiR_3$ wherein each R is the same or different and represents hydrogen, $C_{1-15}$ alkyl or $C_{2-15}$ alkenyl; $C_{1-15}$ alkylthio; $C_{2-15}$ alkenylthio; $C_{6-14}$ arylthio; $C_{6-14}$ aryl and 5- to 10-membered heteroaryl, wherein the groups $C_{6-14}$ aryl and 5- to 10-membered heteroaryl, when present, are substituted with from one to five substituents which are themselves unsubstituted and are selected from the group consisting of $C_{1-15}$ alkyl, $C_{2-15}$ alkenyl, $C_{1-15}$ alkoxy and $C_{2-15}$ alkenyloxy;

with the proviso that where CORE is the non-metallic core, then X is an at least partially conjugated dendritic molecular structure comprising at least one linking group.

2. A dendrimer as claimed in claim 1 and having formula (II):

CORE-[B[X]$_b$]$_a$                             (II)

wherein:
CORE is:
(a) a group containing a metal ion, which group comprises a metal cation and attached ligands, wherein the attached ligands form part of the CORE and include a bidentate ligand, which bidentate ligand comprises a carbocyclic ring which acts as a carbon donor and a heterocyclic ring which acts as a heteroatom donor, wherein the carbocyclic ring and the heterocyclic ring are directly linked to each other by a single bond, wherein the carbocyclic ring is a phenyl group, and the heterocyclic ring is a heteroaryl group which is a 5- or 6-membered aromatic ring containing at least one heteroatom, and wherein at least one dendron of said formula B-[X]$_b$ is bound to said bidentate ligand, provided that the carbocyclic ring which is a phenyl group and the heterocyclic ring which is a heteroaryl group are otherwise unsubstituted, and provided that when at least one dendron of formula B-[X]$_b$ is bound to the carbocyclic ring, each dendron is bound to a meta- or para-position of the ring relative to the bond between the ring and the metal, and provided that when at least one dendron of formula B-[X]$_b$ is bound to the heterocyclic ring and the heterocyclic ring is a six-membered ring, each dendron is bound to a meta- or para-position of the ring relative to the bond between the ring and the metal, or
(b) a non-metallic core which is a non-polymeric organic group;
B is a phenyl ring;
a is an integer of from 3 to 8;
b is an integer of from 3 to 5;
each X is the same or different and represents an aryl or heteroaryl ring, or represents an at least partially conjugated dendritic molecular structure comprising at least one branching group and optionally at least one linking group, the branching groups being selected from the group consisting of aryl and heteroaryl groups and nitrogen atoms, and the linking groups being selected from the group consisting of aryl, heteroaryl, vinyl and acetylenyl groups, said at least one branching group being bonded to three or more groups, and said at least one linking group being bonded to two groups, said dendritic molecular structure terminating at its distal points in aryl and/or heteroaryl groups;

wherein the dendrimer further comprises one or more surface groups, wherein the one or more surface groups are as defined in claim 1;

with the proviso that where CORE is the non-metallic core, then X is an at least partially conjugated dendritic molecular structure comprising at least one linking group.

3. A dendrimer as claimed in claim 1 wherein the surface groups are such as to allow solution processing and/or to allow the dendrimer to be photo-patterned.

4. A dendrimer as claimed in claim 1 wherein each X represents an at least partially conjugated dendritic molecular structure.

5. A dendrimer as claimed in claim 1 wherein at least one X represents a $C_{6-14}$ aryl group which is substituted by one or more surface groups, wherein the one or more surface groups are as defined in claim 1.

6. A dendrimer as claimed in claim 1 and having the formula (V):

CORE-[B-([X]$_b$-[S]$_h$)]$_a$                       (V)

wherein:
a, b, B, X and CORE are as defined in claim 1;
each S is the same or different and represents a surface group as defined in claim 1; and
h is an integer of from 1 to 200.

7. A dendrimer as claimed in claim 1 and having the formula (VI):

CORE-[B-([X$_1$-[X$_2$-[X$_3$-[X$_4$-[X$_5$]$_f$]$_e$]$_d$]$_c$]$_b$-[S]$_h$)]$_a$     (VI)

wherein:
a, b, CORE and B are as defined in claim 1;
c is zero or an integer of from 2 to 6;
when c is not zero, d is zero or an integer of from 2 to 6;
when d is not zero, e is zero or an integer of from 2 to 6;
when e is not zero, f is zero or an integer of from 2 to 6; and
each of $X_1$, $X_2$, $X_3$, $X_4$ and $X_5$, where present, is the same or different and represents a group of formula [L$_g$-B'] wherein:
each L is the same or different and represents a linking group selected from the group consisting of aryl, heteroaryl, vinyl and acetylenyl groups;
g is zero or one, wherein when g is zero L is absent; and
each B' is the same or different and represents a group selected from the group consisting of aryl and heteroaryl groups and nitrogen atoms;
each S is the same or different and represents a surface group as defined in claim 1; and
h is an integer of from 1 to 200;
with the proviso that where CORE is said non-metallic core at least one group L is present.

8. A dendrimer according to claim 1 wherein CORE represents a group of formula MW$_w$Y$_z$, in which M represents a metal cation, w represents an integer of 1 or more, each W is the same or different and represents a bi-dentate coordinating group comprising a carbocyclic ring which acts as a carbon donor and a heterocyclic ring which acts as a heteroatom donor, wherein the carbocyclic ring and the heterocyclic ring are directly linked to each other by a single bond, wherein the carbocyclic ring is a phenyl group, and the heterocyclic ring is a heteroaryl group which is a 5- or 6-membered aromatic ring containing at least one heteroatom, and wherein at least one dendron of said formula B-[X]$_b$ is bound to said bidentate coordinating group, provided that the carbocyclic ring which is a phenyl group and the heterocyclic ring which is a heteroaryl group are otherwise unsubstituted, and provided that when at least one dendron of formula B-[X]$_b$ is bound to the carbocyclic ring, each dendron is bound to a meta- or para-position of the ring relative to the bond between the ring and the metal, and provided that when at least one dendron of formula B-[X]$_b$ is bound to the heterocyclic ring and the heterocyclic ring is a six-membered ring, each dendron is bound to a meta- or para-position of the ring relative to the bond between the ring and the metal, z represents 0 or an integer of 1 or more, and each Y is the same or different and represents a coordinating group, the total of (b·w)+(c·z) being equal to the number of coordination sites on M, wherein b is the number of coordination sites on W and c is the number of coordination sites on Y.

9. A dendrimer as claimed in claim 1 which is luminescent in the solid state.

10. A dendrimer as claimed in claim 9 wherein the dendrimer is phosphorescent in the solid state.

11. A dendrimer of formula (I)

[DENDRON$^1$]$_x$-CORE[B-[X]$_b$]$_a$     (I)

wherein:
CORE is:
(a) a group containing a metal ion, which group comprises a metal cation and attached ligands, wherein the attached ligands form part of the CORE and include a bidentate ligand, which bidentate ligand comprises a carbocyclic ring which acts as a carbon donor and a heterocyclic ring which acts as a heteroatom donor, wherein the carbocyclic ring and the heterocyclic ring are directly linked to each other by a single bond, wherein the carbocyclic ring is a phenyl group, and the heterocyclic ring is a heteroaryl group which is a 5- or 6-membered aromatic ring containing at least one heteroatom, and wherein at least one dendron of said formula B-[X]$_b$ is bound to said bidentate ligand, provided that the carbocyclic ring which is a phenyl group and the heterocyclic ring which is a heteroaryl group are otherwise unsubstituted, and provided that when at least one dendron of formula B-[X]$_b$ is bound to the carbocyclic ring, each dendron is bound to a meta- or para-position of the ring relative to the bond between the ring and the metal, and provided that when at least one dendron of formula B-[X]$_b$ is bound to the heterocyclic ring and the heterocyclic ring is a six-membered ring, each dendron is bound to a meta- or para-position of the ring relative to the bond between the ring and the metal, or
(b) a non-metallic core which is a non-polymeric organic group;

B is a phenyl ring;
a is an integer of from 3 to 8;
b is an integer of from 3 to 5;
x is zero or an integer of from 1 to 7;
each X is the same or different and represents an aryl or heteroaryl ring, or represents an at least partially conjugated dendritic molecular structure comprising at least one branching group and optionally at least one linking group, the branching groups being selected from the group consisting of aryl and heteroaryl groups and nitrogen atoms, and the linking groups being selected from the group consisting of aryl, heteroaryl, vinyl and acetylenyl groups, said branching groups being bonded to three or more groups, and said linking groups being bonded to two groups, said dendritic molecular structure terminating at its distal points in aryl and/or heteroaryl groups; and DENDRON$^1$ represents an at least partially conjugated dendritic molecular structure comprising at least one branching group and optionally at least one linking group, the branching groups being selected from the group consisting of aryl and heteroaryl groups and nitrogen atoms, and the linking groups being selected from the group consisting of aryl, heteroaryl, alkyleneoxy, vinyl and acetylenyl groups, said branching groups being bonded to three or more groups, and said linking groups being bonded to two groups, said dendritic molecular structure terminating at its distal points in aryl and/or heteroaryl groups;

with the proviso that where CORE is said non-metallic core, then X is an at least partially conjugated dendritic molecular structure comprising at least one linking group, and with the proviso that when at least one X is an at least partially conjugated dendritic molecular structure, at least one surface group is bonded to an aryl and/or heteroaryl group which terminates said dendritic structure, wherein the at least one surface group is selected from the group consisting of hydroxy; $C_{1-15}$ alkyl; $C_{2-15}$ alkenyl; amine; $C_{1-15}$ alkylamine; di($C_{1-15}$)alkylamine; COOR wherein R is hydrogen or $C_{1-15}$ alkyl; $C_{1-15}$ alkoxy; $C_{2-15}$alkenyloxy; $C_{6-10}$ aryloxy; O$_2$SR wherein R is $C_{1-15}$ alkyl or $C_{2-15}$ alkenyl; SiR$_3$ wherein each R is the same or different and represents hydrogen, $C_{1-15}$ alkyl or $C_{2-15}$ alkenyl; $C_{1-15}$ alkylthio; $C_{2-15}$ alkenylthio; $C_{6-14}$ arylthio; $C_{6-14}$ aryl and 5- to 10-membered heteroaryl, wherein the groups $C_{6-14}$ aryl and 5- to 10-membered heteroaryl, when present, are substituted with from one to five substituents which are themselves unsubstituted and are selected from the group consisting of $C_{1-15}$ alkyl, $C_{2-15}$ alkenyl, $C_{1-15}$alkoxy and $C_{2-15}$ alkenyloxy, and with the proviso that the dendrimer is not fac-tris[2-{5-[(2,3,4,5-tetraphenyl)phenyl]phenyl}-pyridinato-N, C$^2$]iridium(III).

12. A blend comprising a dendrimer as claimed in claim 1.

13. A blend as claimed in claim 12 wherein the blend further comprises one or more other dendrimers and/or polymers and/or molecular materials.

14. A blend comprising a first dendrimer as claimed in claim 1 wherein CORE is said group containing a metal ion, and a second dendrimer as claimed in claim 1 wherein CORE is said non-metallic core which is a non-polymeric organic group, and wherein the dendrons of the first dendrimer and second dendrimer have the same dendritic structure.

15. A semiconducting device which comprises at least one layer that contains a dendrimer as defined in claim 1.

16. A device according to claim 15 which is a photodiode, a solar cell, field effect transistor, solid state triode, a light emitting device or a light emitting diode.

17. A device according to claim 16 wherein the device is a light emitting device and the dendrimer is in a light emitting layer.

18. A device according to claim 17 which comprises in addition to the light emitting layer at least one charge transporting and/or injecting layer.

19. A device according to claim 18 which comprises an electron transporting layer between the light emitting layer and a cathode.

20. A device according to claim 15 wherein said at least one layer comprises a blend comprising one or more other dendrimers and/or polymers and/or molecular materials.

21. A device according to claim 15 wherein the layer has an organometallic dendrimer which has been deposited by solution processing.

22. A dendrimer as claimed in claim 1 wherein CORE is:
(a) the group containing a metal ion, wherein the carbocyclic ring of the bidentate ligand is a phenyl group and the heterocyclic ring of the bidentate ligand is a pyridine group and the bidentate ligand is 2-phenylpyridine, provided that when at least one dendron of formula B-$[X]_b$ is bound to the phenyl group, each dendron is bound to a meta- or para-position of the phenyl relative to the bond between the ring and the metal, and when at least one dendron of formula B-$[X]_b$ is bound to the pyridine group, each dendron is bound to a meta- or para-position of the ring relative to the bond between the ring and the metal, provided that the phenyl and pyridine groups are otherwise unsubstituted; or
(b) said non-metallic core which is a non-polymeric organic group.

23. A dendrimer as claimed in claim 11 wherein CORE is:
(a) the group containing a metal ion, wherein the carbocyclic ring of the bidentate ligand is a phenyl group and the heterocyclic ring of the bidentate ligand is a pyridine group and the bidentate ligand is 2-phenylpyridine, provided that when at least one dendron of formula B-$[X]_b$ is bound to the phenyl group, each dendron is bound to a meta- or para-position of the ring relative to the bond between the ring and the metal, and when at least one dendron of formula B-$[X]_b$ is bound to the pyridine group, each dendron is bound to a meta- or para-position of the ring relative to the bond between the ring and the metal, provided that the phenyl and pyridine groups are otherwise unsubstituted; or
(b) the non-metallic core which is a non-polymeric organic group.

* * * * *

UNITED STATES PATENT AND TRADEMARK OFFICE
CERTIFICATE OF CORRECTION

PATENT NO. : 9,078,330 B2
APPLICATION NO. : 11/886450
DATED : July 7, 2015
INVENTOR(S) : Paul Leslie Burn, Ifor David William Samuel and Neil Cumpstey It is certified that error appears in the above-identified patent and that said Letters Patent is hereby corrected as shown below:

In the specification

Column 2, line 35 "surface groups;" should be -- surface groups; with the proviso that where CORE is a non-metallic core, then X is an at least partially conjugated dendritic molecular structure comprising at least one linking group. In an alternative embodiment the dendrimer of formula (I) need not comprise one or more surface groups. In this alternative embodiment, preferably a is from 3 to 8. Furthermore, in this embodiment preferably the dendrimer is not fac-tris[2-{5-[(2,3,4,5-tetraphenyl)phenyl]phenyl}pyridinato-N1,C2]iridium(III), that is, a dendrimer of the formula: --

Column 4, line 36 "-C(O)R" should be -- -C(O)2R --

Signed and Sealed this
First Day of December, 2015

Michelle K. Lee
*Director of the United States Patent and Trademark Office*